(12) United States Patent
Meier-Davis et al.

(10) Patent No.: US 9,913,812 B2
(45) Date of Patent: Mar. 13, 2018

(54) METHODS FOR THE TREATMENT OF SKIN NEOPLASMS

(71) Applicant: TEIKOKU PHARMA USA, INC., San Jose, CA (US)

(72) Inventors: Susan Meier-Davis, San Jose, CA (US); Jianye Wen, Palo Alto, CA (US); Richard D. Hamlin, Newark, CA (US)

(73) Assignee: Teikoku Pharma USA, Inc., San Jose, CA (US)

( * ) Notice: Subject to any disclaimer, the term of this patent is extended or adjusted under 35 U.S.C. 154(b) by 574 days.

(21) Appl. No.: 13/668,065

(22) Filed: Nov. 2, 2012

(65) Prior Publication Data

US 2013/0302441 A1    Nov. 14, 2013

Related U.S. Application Data

(60) Provisional application No. 61/557,632, filed on Nov. 9, 2011.

(51) Int. Cl.
| | |
|---|---|
| *A61K 31/135* | (2006.01) |
| *A61K 33/24* | (2006.01) |
| *A61K 45/06* | (2006.01) |
| *A61K 31/27* | (2006.01) |
| *A61K 9/70* | (2006.01) |

(52) U.S. Cl.
CPC .......... *A61K 31/135* (2013.01); *A61K 9/7061* (2013.01); *A61K 31/27* (2013.01); *A61K 33/24* (2013.01); *A61K 45/06* (2013.01)

(58) Field of Classification Search
CPC .... A61K 31/135; A61K 9/7061; A61K 31/27; A61K 33/24; A61K 45/06

USPC ........................................................ 424/649
See application file for complete search history.

(56) References Cited

U.S. PATENT DOCUMENTS

| | | | |
|---|---|---|---|
| 4,452,808 | A | 6/1984 | Gallagher |
| 4,588,740 | A | 5/1986 | Gallagher |
| 4,824,860 | A | 4/1989 | Owen |
| 4,912,126 | A | 3/1990 | Owen |
| 5,176,916 | A | 1/1993 | Yamanaka et al. |
| 5,387,612 | A | 2/1995 | Youdim et al. |
| 5,391,406 | A | 2/1995 | Ramharack et al. |
| 5,422,123 | A | 6/1995 | Conte et al. |
| 5,453,446 | A | 9/1995 | Youdim et al. |

(Continued)

FOREIGN PATENT DOCUMENTS

| | | | | |
|---|---|---|---|---|
| EP | 1 049 478 B1 | * | 4/2002 | ............. A61K 31/13 |
| EP | 2011488 | | 1/2009 | |

(Continued)

OTHER PUBLICATIONS

Medline Plus—US. National Library of Medicine NIH National Institutes of Health, Rasagiline, publication Apr. 15, 2011, http://www.nlm.nih.gov/medlineplus/druginfo/meds/a606017.html#why.*

(Continued)

*Primary Examiner* — Sreenivasan Padmanabhan
*Assistant Examiner* — Y Jeanmarie Z Calvillo
(74) *Attorney, Agent, or Firm* — Otto C. Guedelhoefer IV; Bret E. Field; Bozicevic, Field & Francis LLP

(57) ABSTRACT

Methods of treating skin neoplasms using a monoamine oxidase inhibitor, e.g., a propynylaminoindan (such as rasagiline) are provided. Pharmaceutical compositions and kits comprising monoamine oxidase inhibitors are also provided.

26 Claims, 15 Drawing Sheets

(56) References Cited

U.S. PATENT DOCUMENTS

| | | | |
|---|---|---|---|
| 5,457,133 A | 10/1995 | Youdim et al. | |
| 5,462,746 A | 10/1995 | Wolter et al. | |
| 5,519,061 A | 5/1996 | Youdim et al. | |
| 5,532,415 A | 7/1996 | Youdim et al. | |
| 5,543,151 A | 8/1996 | Shirai et al. | |
| 5,576,353 A | 11/1996 | Youdim et al. | |
| 5,599,991 A | 2/1997 | Youdim et al. | |
| 5,650,165 A | 7/1997 | Akemi et al. | |
| 5,668,181 A | 9/1997 | Youdim et al. | |
| 5,683,710 A | 11/1997 | Akemi et al. | |
| 5,744,500 A | 4/1998 | Youdim et al. | |
| 5,786,390 A | 7/1998 | Youdim et al. | |
| 5,807,570 A | 9/1998 | Chen et al. | |
| 5,830,497 A | 11/1998 | Yamanaka et al. | |
| 5,891,923 A | 4/1999 | Youdim et al. | |
| 6,126,968 A | 10/2000 | Peskin et al. | |
| 6,132,761 A | 11/2000 | Muraoka et al. | |
| 6,146,656 A | 11/2000 | Hori et al. | |
| 6,198,017 B1 | 3/2001 | Basedow et al. | |
| 6,218,421 B1 | 4/2001 | King | |
| 6,231,885 B1 | 5/2001 | Carrara | |
| 6,262,330 B1 | 7/2001 | Fujisawa et al. | |
| 6,300,365 B1 | 10/2001 | Holman | |
| 6,316,504 B1 | 11/2001 | Youdim et al. | |
| 6,528,685 B2 | 3/2003 | Cohen et al. | |
| 6,562,363 B1 | 5/2003 | Mantelle et al. | |
| 6,630,514 B2 | 10/2003 | Youdim et al. | |
| 6,638,528 B1 | 10/2003 | Kanios | |
| 6,689,379 B1 | 2/2004 | Bracht | |
| 6,809,120 B1 * | 10/2004 | Warrington | A61K 31/505 514/110 |
| 6,929,801 B2 | 8/2005 | Klose et al. | |
| 6,936,661 B2 | 8/2005 | Koch et al. | |
| 6,956,060 B2 | 10/2005 | Youdim et al. | |
| 7,070,808 B2 | 7/2006 | Govil et al. | |
| 7,150,881 B2 | 12/2006 | Govil et al. | |
| 7,175,853 B1 | 2/2007 | Bracht | |
| 7,220,473 B2 | 5/2007 | Beier et al. | |
| 7,335,379 B2 | 2/2008 | Carrara et al. | |
| 7,375,249 B2 | 5/2008 | Boulton et al. | |
| 7,378,439 B2 | 5/2008 | Tarur et al. | |
| 7,396,860 B2 | 7/2008 | Blaugrund et al. | |
| 7,491,847 B2 | 2/2009 | Frenkel et al. | |
| 7,572,834 B1 | 8/2009 | Sterling et al. | |
| 7,598,420 B1 | 10/2009 | Sterling et al. | |
| 7,638,140 B2 | 12/2009 | Govil et al. | |
| 2003/0212085 A1 | 11/2003 | McCall et al. | |
| 2004/0013620 A1 | 1/2004 | Klose et al. | |
| 2004/0127577 A1 * | 7/2004 | Blaugrund et al. | 514/657 |
| 2004/0253299 A1 | 12/2004 | Beier et al. | |
| 2005/0175680 A1 | 8/2005 | Morgan et al. | |
| 2005/0186141 A1 | 8/2005 | Gonda | |
| 2005/0187283 A1 | 8/2005 | Drago | |
| 2005/0191348 A1 | 9/2005 | Youdim et al. | |
| 2005/0245617 A1 | 11/2005 | Meyerson et al. | |
| 2005/0267176 A1 | 12/2005 | Barberich | |
| 2006/0078604 A1 | 4/2006 | Kanios et al. | |
| 2006/0188581 A1 | 8/2006 | Peskin et al. | |
| 2007/0026054 A1 | 2/2007 | Theobald et al. | |
| 2007/0078172 A1 | 4/2007 | McElroy et al. | |
| 2007/0093495 A1 | 4/2007 | Ruggero et al. | |
| 2007/0225379 A1 | 9/2007 | Carrara et al. | |
| 2007/0254941 A1 | 11/2007 | Kumar et al. | |
| 2008/0004329 A1 | 1/2008 | Jamieson et al. | |
| 2008/0089859 A1 | 4/2008 | Homan | |
| 2008/0161408 A1 | 7/2008 | Frenkel et al. | |
| 2008/0220092 A1 | 9/2008 | Dipierro et al. | |
| 2008/0292708 A1 | 11/2008 | Stephanelli et al. | |
| 2009/0035377 A1 | 2/2009 | Houze | |
| 2009/0043111 A1 | 2/2009 | Liu | |
| 2009/0062400 A1 | 3/2009 | Oron et al. | |
| 2009/0076160 A1 | 3/2009 | Lendvai et al. | |
| 2009/0136549 A1 * | 5/2009 | Lin et al. | 424/400 |
| 2009/0136555 A1 | 5/2009 | Crowley et al. | |
| 2009/0318564 A1 | 12/2009 | Frenkel et al. | |
| 2010/0010095 A1 | 1/2010 | Frenkel | |
| 2010/0016442 A1 | 1/2010 | Cohen et al. | |
| 2010/0029987 A1 | 2/2010 | Allegrini et al. | |
| 2010/0087768 A1 | 4/2010 | Forlano et al. | |
| 2013/0058873 A1 * | 3/2013 | Jefferies et al. | 424/9.34 |

FOREIGN PATENT DOCUMENTS

| | | | |
|---|---|---|---|
| JP | 2004-519409 A | 7/2004 | |
| WO | WO199840102 | 9/1998 | |
| WO | 2000033812 | 6/2000 | |
| WO | 2004012730 | 2/2004 | |
| WO | WO2006048242 A2 | 5/2006 | |
| WO | WO2007098264 A2 * | 2/2007 | A61K 31/13 424/649 |
| WO | 2009030351 | 3/2009 | |
| WO | 2009152777 | 12/2009 | |

OTHER PUBLICATIONS

Ricotti, et al., Med. Clin. N. Am. 93 (2009) 1241-1264.*
Abassi, et al., British Journal of Pharmacology (2004) 143, 371-378.*
Genentech Document on Melanoma—http://www.skincancer.org/skin-cancer-information/melanoma.*
Lecht, et al., Therapeutics and Clinical Risk Management 2007:3(3) 467-474.*
Ferreira, J. J., et al. "Skin cancer and Parkinson's disease." Movement Disorders vol. 25, Issue 2, Nov. 2, 2010, pp. 139-148.
Nayak, et. al. "Rasagiline in treatment of Parkinson's disease." Neuropsychiatr Dis Treat. Feb. 2008; 4(1): 23-32.
Strupp, M. "Parkinson's disease I: glucocerebrosidase mutations, family history of melanoma and questionable effects of rasagiline." J Neurol. Dec. 2009; 256 (12):2111-4.
Meier-Davis, et al., "Comparison of oral and transdermal administration of rasagiline mesylate on human melanoma tumor growth in vivo"., Cutaneous and Ocular Toxicology, 2012; pp. 1-6, Informa Healthcare USA, Inc., ISSN 1556-9527 print.
Szende et al., Apoptotic and antiapoptotic effect of (-)deprenyl and (-)-desmethyl-deprenyl on human cell lines, Neurobiology (Bp) (Jan. 2000), 8(3-4):249-255.

* cited by examiner

METHODS FOR THE TREATMENT OF SKIN NEOPLASMS

CROSS-REFERENCE TO RELATED APPLICATIONS

Pursuant to 35 U.S.C. § 119(e), this application claims priority to the filing date of U.S. Provisional Patent Application Ser. No. 61/557,632, filed on Nov. 9, 2011, the disclosure of which application is herein incorporated by reference.

INTRODUCTION

Skin neoplasms may occur in many different parts of the body. Symptoms associated with skin neoplasms include, e.g., changes in the color and/or appearance of the skin, such as the formation of a colored patch of skin, the formation of a new growth, and/or the formation of a sore or ulcer that resists healing. Symptoms may also include changes in existing skin structures, such as moles, and may include, e.g., changes in the border of the mole, such as formation of jagged edges around the mole, enlargement of the mole, and/or changes in the elevation of the mole.

Skin neoplasms can originate in any of the various layers of the skin, e.g., in the epidermis, dermis, or hypodermis. If left untreated, skin neoplasms can grow in size within a particular layer of the skin, and can also penetrate into other layers of the skin. Eventually, some of the cells in the skin neoplasm can break off from the original growth and enter the blood stream or the lymphatic system, allowing the skin neoplasm cells to travel to other parts of the body and form satellite tumors. Such tumors typically form in areas of the body with a high blood supply, such as the brain, bones, and liver. Once established, the satellite tumors can cause significant damage in these locations.

Skin neoplasms are one of the most prevalent diseases in the United States, with over 3.5 million cases diagnosed annually (Rogers, H W, Weinstock, M A, Harris, A R, et al. *Incidence estimate of nonmelanoma skin cancer in the United States,* 2006. Arch Dermatol 2010; 146(3):283-287). Melanoma, for example, is one of the more deadly forms of cancer, accounting for approximately 75% of deaths due to skin cancer (American Cancer Society, *Cancer Facts and Figures* 2010).

Treatment of skin neoplasms generally depends on the specific type of neoplasm as well as the location of the neoplasm on the patient's body, and may include surgical removal (e.g., curettage and desiccation, large-scale surgical removal of tumors), chemotherapy (e.g., topical administration of chemotherapeutic agents), cryotherapy (e.g., freezing and removing a tumor), and/or radiation therapy (e.g., external beam radiotherapy and/or brachytherapy).

SUMMARY

Methods of treating skin neoplasms are provided. Aspects of the methods include administering to a subject an effective amount of a monoamine oxidase inhibitor, e.g., a propynylaminoindan, such as rasagiline. Pharmaceutical compositions and kits comprising monoamine oxidase inhibitors are also provided.

Methods of the present disclosure include treating a subject having a skin neoplasm, the method comprising administering to the subject an effective amount of a monoamine oxidase inhibitor to treat the subject for the skin neoplasm. Target skin neoplasms may be melanocyte-derived skin neoplasms, such as a malignant melanoma. The subject being treated may be one that has been diagnosed with the skin neoplasm. Subjects suitable for treatment via methods disclosed herein include mammals, e.g., humans.

In some instances, the monoamine oxidase inhibitor is a propynylaminoindan or a pharmaceutically acceptable salt thereof. The propynylaminoindan may have the formula:

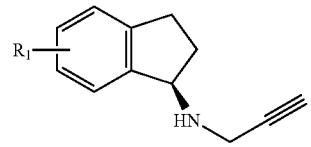

wherein $R_1$ is H, $-OR_2$, or

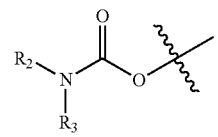

wherein $R_2$ is $C_1$-$C_4$ alkyl, and $R_3$ is H or $C_1$-$C_4$ alkyl. In some embodiments, the propynylaminoindan is rasagiline, or a pharmaceutically acceptable salt thereof.

The amount of monoamine oxidase inhibitor administered to the subject may vary, ranging in some instances from 0.5 mg/kg/day to 30 mg/kg/day, such as 5 mg/kg/day to 25 mg/kg/day, including 10 mg/kg/day to 20 mg/kg/day, e.g., 12.5 to 17.5 mg/kg/day.

Routes of administration may vary. In some embodiments, the monoamine oxidase inhibitor is enterally, e.g., orally, administered to the subject. In some embodiments, the monoamine oxidase inhibitor is administered to the subject by topically applying a composition comprising the monoamine oxidase inhibitor to the skin of the subject.

Compositions employed in various embodiments of the described methods include a sufficient amount of monoamine oxidase inhibitor to provide for a target administration amount, e.g., as described above. In some instances, the composition comprises an amount of the monoamine oxidase inhibitor ranging from 0.5 mg to 1 g. In some embodiments, the composition is a solid composition configured to cover a topical area, where the topical area may range in size from 10 cm² to 200 cm², such as 20 cm² to 150 cm², including 40 cm² to 140 cm². Where desired, the amount of the monoamine oxidase inhibitor in such compositions may range from 5 mg to 90 mg, e.g., from 10 mg to 60 mg, including from 15 mg to 30 mg.

Where topical compositions are employed, the composition may be applied to the skin of the subject for a period of time sufficient to treat the subject, e.g., 1 hour or longer, 1 day or longer, 3 days or longer, 1 week or longer, and in some instances ranging from 1 hour to 1 week, such as 10 hours to 5 days, e.g., 1 day to 3 days.

Where desired, the methods disclosed herein may further include administering an anti-neoplastic agent to the subject in combination with the monoamine oxidase inhibitor. The anti-neoplastic agent may vary, where anti-neoplastic agents of interest include, but are not limited to, alkylating agents, platinum compounds, anti-metabolic agents, anthracyclines, cytotoxic antibiotics, monoclonal antibodies, kinase inhibitors, plant alkaloids, terpenoids, topoisomerase inhibitors, vinca alkaloids, taxanes, podophyllotoxins, epipodophyllotoxins, and combinations thereof.

Aspects of the invention also include pharmaceutical compositions comprising a monoamine oxidase inhibitor (e.g., as described above) and an anti-neoplastic agent (e.g., as described above), where the compositions may be configured for use in methods such as those summarized above.

Also provided are kits comprising a monoamine oxidase inhibitor (e.g., as described above) and an anti-neoplastic agent (e.g., as described above).

DETAILED DESCRIPTION

Figure 1:
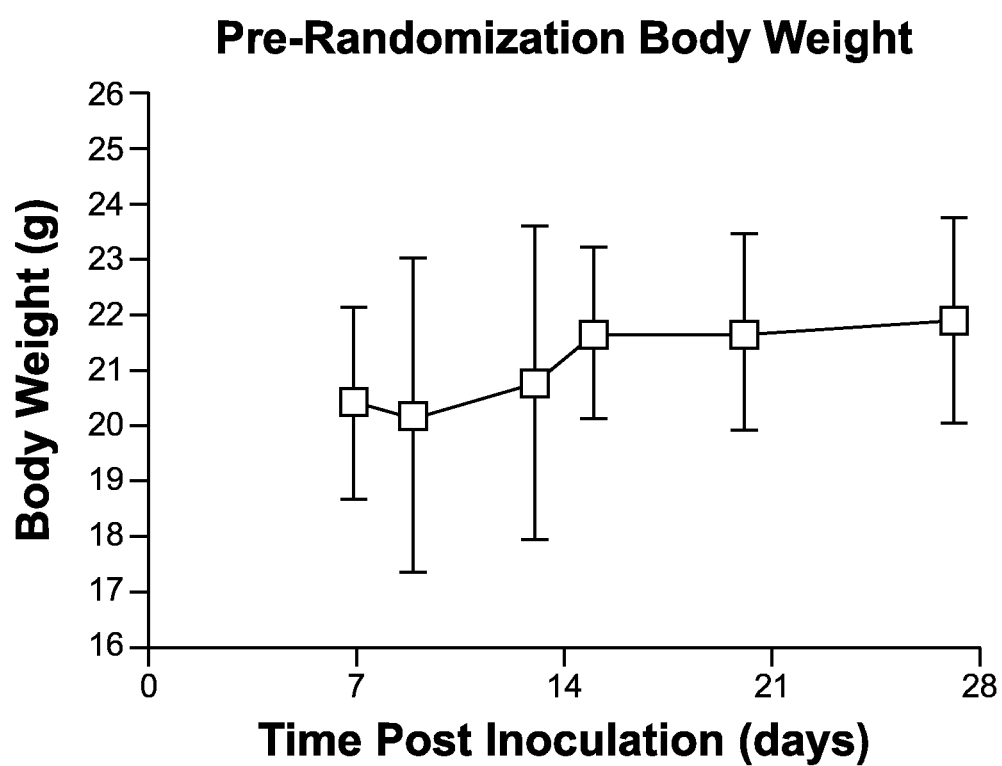
FIG. 1 is a graph of the body weights of the animals following tumor inoculation, prior to assignment to treatment groups. Data points represent the mean body weights and error bars represent standard deviations and lines are connecting lines between mean values.

Methods of treating skin neoplasms using a monoamine oxidase inhibitor, e.g., a propynylaminoindan (such as rasagiline) are provided. Pharmaceutical compositions and kits comprising monoamine oxidase inhibitors are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include treating a subject for a skin neoplasm by administering to the subject an effective amount of a monoamine oxidase inhibitor. The term "skin neoplasm," as used herein, refers to any skin growth having any degree of malignancy, and may include neoplasms in locations such as the eye or bowel in addition to the visible, external portions of the skin. Exemplary skin neoplasms include, but are not limited to: keratinocytic neoplasms, such as basal cell carcinoma, squamous cell carcinoma, Bowen's disease, bowenoid papulosis, actinic keratosis, and keratoacanthoma; melanocytic neoplasms, including all types of melanoma, such as superficial spreading melanoma, nodular melanoma, lentigo melanoma, acral-lentiginous melanoma, desmoplastic melanoma, nevoid melanoma, and amelanotic melanoma; appendageal neoplasms; soft tissue neoplasms; neural neoplasms; and cutaneous neoplasms. Skin neoplasms amenable to treatment using the methods of the present disclosure include benign, pre-malignant, malignant, and/or metastatic skin neoplasms.

By "treating," "treatment," or "treat" is meant that at least an amelioration of the symptoms associated with the condition afflicting the subject is achieved, where amelioration is used in a broad sense to refer to at least a reduction in the magnitude of a parameter, e.g., a symptom, associated with the condition being treated. As such, treatment includes a broad spectrum of situations ranging from slowing, delaying, or halting progression of a pathological condition and/or a related symptom, up to and including completely eliminating the condition, along with any associated symptoms. Treatment therefore includes situations where the condition, or at least a symptom associated therewith, is completely inhibited, e.g., prevented from happening, or stopped, e.g., terminated, such that the subject no longer suffers from the condition, or at least the symptoms that characterize the condition. Treatment also includes situations where the progression of the condition, or at least the progression of a symptom associated therewith, is slowed, delayed, or halted. In such cases, a subject might still have residual symptoms associated with the pathological condition, but any increase in the severity or magnitude of the symptoms is slowed, delayed, or prevented. In some instances, treatment results in at least a delay in tumor growth (i.e., a reduction in tumor growth rate) in a subject as compared to a suitable control, where in some instances the delay may be 2% or longer, e.g., 5% or longer, such as 10%, 25%, 50% or 100% or longer.

As summarized above, in practicing methods of the invention an effective amount of a monoamine oxidase inhibitor (MAOI) is administered to the subject. Monoamine oxidase inhibitors may include reversible and irreversible inhibitors of MAO isoforms A (MAO-A) and B (MAO-B). Inhibitors of MAO-A include, but are not limited to, Brofaromine (Consonar®), Metralindole (Inkazan®), Minaprine (Cantor®), Moclobemide (Aurorix®, Manerix®), Pirlindole (Pirazidol®), and Toloxatone (Humoryl®). Inhibitors of MAO-B include, but are not limited to, Lazabemide (Pakio®, Tempium®), Pargyline (Eutonyl®), Rasagiline (Azilect®), and Selegiline (Deprenyl®, Eldepryl®, Emsam®).

In some instances, the inhibitor is a propynylaminoindan compound, e.g., a compound having the formula:

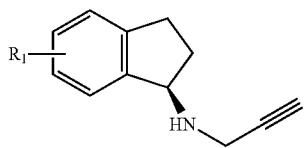

wherein $R_1$ is H, $-OR_2$, or

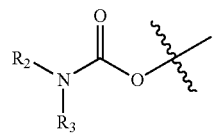

wherein $R_2$ is $C_1$-$C_4$ alkyl, and $R_3$ is H or $C_1$-$C_4$ alkyl. In some instances, the propynylaminoindan compound is N-propargyl-1-aminoindan (i.e., rasagiline, trade name Azilect®).

A given MAOI compound may be employed as a free base or pharmaceutically acceptable derivative thereof. Any pharmaceutically acceptable derivative of the compounds disclosed herein may be used in the methods of the present disclosure, including, e.g., pharmaceutically acceptable salts. In some embodiments, a mesylate salt of a compound disclosed herein may be used, e.g., rasagiline mesylate.

In the methods of the present disclosure, the amount of a MAOI compound administered to a subject is sufficient to achieve a desired effect or treatment. The amount administered may vary depending on the goal of the administration, the health and physical condition of the subject being treated, the subject's age, the degree of resolution desired, the formulation and/or activity of the subject composition, the treating clinician's assessment of the medical situation, the body weight/mass of the subject, as well as the severity of the disease or condition being treated, among other relevant factors. The dosage may also be determined based on the existence, nature, extent, and severity of any adverse side-effects that might accompany the administration of a particular composition.

It is expected that the dosage will fall in a relatively broad range that can be determined through routine trials. For example, in some embodiments, the dosage is not more than an amount that could be otherwise irreversibly toxic to the subject (i.e., the maximum tolerated dose). In other cases, the dosage is near or even well below the toxic threshold, but is still an effective amount to treat the target disease or condition. In some embodiments, the dosage ranges from 0.5 mg/kg/day or more, up to 5 mg/kg/day or more, up to 10 mg/kg/day or more, up to 12.5 mg/kg/day or more, up to 15 mg/kg/day or more, up to 17.5 mg/kg/day or more, up to 20 mg/kg/day or more, up to 25 mg/kg/day or more, or up to 30 mg/kg/day.

In practicing the methods of the present disclosure, the MAOI may be administered to the subject according to any convenient administration protocol. As such, one or more of the MAOIs disclosed herein may be administered to a subject via a suitable route of administration and in a sufficient amount to effectively treat a skin neoplasm. The subject methods are generally used to establish and/or maintain a target concentration of one or more of the subject compounds in the tissues of a subject in order to treat the skin neoplasm. Administration routes of interest include, but are not limited to, transdermal, enteral (e.g., through the gastrointestinal tract of the subject, including oral and rectal administration), and parenteral routes (e.g., intravenous injection, intra-arterial injection, intramuscular injection, or intraosseous infusion). While any convenient administration route may be employed, two administration routes of interest include transdermal and enteral.

In some embodiments, a transdermal composition may be used to administer the MAOI to a subject, i.e., the MAOI is transdermally administered to the subject. In such instances, a transdermal formulation which includes the MAOI is contacted with a convenient topical site (e.g., skin site) of the subject. Topical sites of interest include both mucosal sites and keratinized skin sites, and therefore include, but are not limited to: mouth, nose, eyes, rectum, vagina, arms, leg, torso, head, etc. The surface area that is covered by the composition following application is sufficient to provide for the desired amount of agent administration, and in some embodiments ranges from 10 $cm^2$ to 200 $cm^2$, such as from 20 $cm^2$ to 150 $cm^2$, and including from 40 $cm^2$ to 140 $cm^2$, e.g., 100 $cm^2$.

In practicing methods of the invention, any convenient transdermal composition may be employed. Transdermal compositions, also known as transdermal patches or skin patches, are adhesive patches containing an active agent, where the compositions are configured to be placed on the skin to deliver the active agent through the skin. Transdermal patches deliver the active agent by percutaneous absorption, which is the absorption of substances through unbroken skin. After a transdermal patch is applied to the skin, the active agent contained in the patch passes through, or permeates the skin and can reach its site of action through systemic blood flow. Alternatively, the transdermal patch may be placed on the desired treatment site such that the medication contained in the patch is delivered topically.

Transdermal compositions may be formulated to provide for multi-day delivery of a therapeutically effective amount of a compound to a subject. By "multi-day delivery" is meant that the composition is formulated to provide a therapeutically effective amount of a compound to the subject when the composition is applied to a skin site of the subject for a period of time that is, e.g., 1 day or longer, such as 2 days or longer, e.g., 3 days or longer, such as 5 days or longer, including 7 days or longer, such as 10 days or longer.

By "therapeutically effective amount" is meant that the compositions, when applied to a skin site of a subject during its intended time of application, e.g., within 7 days of application, provides for a systemic amount of active agent that provides a desired therapeutic activity. In some embodiments, the compositions may provide delivery of a target dosage of active agent ranging from, e.g., 0.5 mg/kg/day or greater over a desired period of time (e.g., 1 week), including 1.0 mg/kg/day or greater, such as 5 mg/kg/day, 10 mg/kg/day, 12.5 mg/kg/day, 15 mg/kg/day, 17.5 mg/kg/day, 20 mg/kg/day, 25 mg/kg/day, 30 mg/kg/day, or greater over a desired time period.

The size (i.e., area) of the transdermal compositions may vary. In certain embodiments, the size of the composition is chosen in view of the transdermal flux rate of the compound and the desired dosage to be achieved. For example, if the transdermal flux rate is 5 μg/$cm^2$/hr and the target dosage is 5 mg/day, then the transdermal composition is chosen to have an area of about 42 $cm^2$. Or for example, if the transdermal flux is 5 μg/$cm^2$/hr and the target dosage is 10 mg/day, then the transdermal patch is chosen have an area of about 84 $cm^2$. In certain embodiments, the compositions have dimensions chosen to cover an area of skin when applied to a skin site that ranges from 10 cm² to 200 cm², such as 20 cm² to 150 cm², including 40 cm² to 140 cm².

In some instances, transdermal compositions of the invention include a matrix layer which contains a propynylaminoindan active agent, and optionally a backing layer and/or release liner. The matrix may include a pressure sensitive adhesive. The terms "pressure sensitive adhesive", "self adhesive", and "self stick adhesive" mean an adhesive that forms a bond when pressure is applied to adhere the adhesive with a surface. In some instances, the adhesive is one in which no solvent, water, or heat is needed to activate the adhesive. For pressure sensitive adhesives, the degree of bond strength is proportional to the amount of pressure that is used to apply the adhesive to the surface. Pressure sensitive adhesives of interest include, but are not limited acrylate polymers, such as acrylate copolymers, including carboxylated acrylate polymers and copolymers. Acrylate copolymers of interest include copolymers of various monomers which may be "soft" monomers, "hard" monomers, and optionally "functional" monomers. Also of interest are blends including such copolymers. The acrylate copolymers can be composed of a copolymer including bipolymer (i.e., made with two monomers), a terpolymer (i.e., made with three monomers), or a tetrapolymer (i.e., made with four monomers), or copolymers made from even greater numbers of monomers. The acrylate copolymers can include cross-linked and non-cross-linked polymers. The polymers can be cross-linked by known methods to provide the desired polymers.

The matrix as described herein may contain a percutaneous absorption enhancer. The percutaneous absorption enhancer may facilitate the absorption of the active agent by the skin of the subject. The percutaneous absorption enhancer may also be referred to as a percutaneous permeation enhancer because it may facilitate not only the percutaneous absorption of the active agent, but also the percutaneous permeation of the active agent through the skin of the subject.

As summarized above, transdermal compositions of interest may include a backing (i.e., support layer). The backing may be flexible to an extent that it can be brought into close contact with a desired topical location of a subject. The backing may be fabricated from a material that it does not absorb the active agent, and does not allow the active agent to be released from the side of the support. The backing may include, but is not limited to, non-woven fabrics, woven fabrics, films (including sheets), porous bodies, foamed bodies, paper, composite materials obtained by laminating a film on a non-woven fabric or fabric, and combinations thereof.

In some embodiments, a release liner is provided on the active agent layer (i.e., matrix), and specifically on a surface of the active agent layer that is distal (i.e. opposite) from the backing layer, if present. The release liner facilitates the protection of the active agent layer. The release liner may be prepared by treating one side of polyethylene-coated wood free paper, polyolefin-coated glassine paper, a polyethylene terephthalate (polyester) film, a polypropylene film, or the like with a silicone treatment.

Transdermal compositions of interest for use methods of the invention include those described in U.S. patent application Ser. No. 13/052,955, filed on Mar. 21, 2011; and U.S. Patent Application No. 61/467,337, filed on Mar. 24, 2011; the entire disclosures of which are hereby incorporated by reference. Other transdermal formulations of interest include, but are not limited to: those described in U.S. Pat. Nos. 7,638,140; 7,220,473; 7,150,881; 7,070,808; 6,929,801; 6,689,379; 6,638,528; 6,630,514; and 5,786,390; the disclosures of the transdermal formulations described therein being incorporated herein by reference.

Following application, a transdermal composition may be maintained at the topical site to which it has been applied for a desired amount of time, e.g., to deliver a desired amount of a compound to the subject. In some embodiments, the period of time that the composition is maintained at the site of application is 1 hour or longer, such as 5 hours or longer, including 10 hours or longer, such as 24 hours or longer, such as 48 hours or longer, e.g., 72 hours or longer, such as 96 hours or longer, such 168 hours or longer, such as 240 hours or longer.

After the transdermal composition has been applied to the skin site for a desired amount of time (i.e., an amount of time sufficient to deliver a target dose of the compound to the subject over a period of time), the composition may be removed from the skin site. A new transdermal composition may be applied at the same or at a different site. The new transdermal composition may be applied to a different skin site to reduce the possible occurrence of skin irritation and/or skin sensitization at the prior site of application. In practicing methods described herein, a single transdermal composition may be applied once, or multiple transdermal compositions may be applied repeatedly over a specified period of time period, e.g., the course of the disease condition being treated, where the dosing schedule when a plurality of compositions are administered over a given time period may be daily, weekly, biweekly, monthly, etc.

For enteral administration, any convenient type of formulation suitable for enteral, e.g., oral or rectal, administration may be employed. In some embodiments, a suitably-formulated composition of the present disclosure (e.g., a pill) may be orally administered to a subject to treat a skin neoplasm. The composition may be administered to the subject repeatedly over a desired period of time (e.g., twice a day for 7 days) in order to establish and/or maintain a desired concentration of the compound in the subject that effectively treats the skin neoplasm.

Compounds of the present disclosure may be formulated for enteral administration through the gastrointestinal tract of the subject, including oral and rectal administration. Oral administration can be accomplished using, e.g., solid formulations, including pills, tablets, capsules, and the like, or, e.g., liquid formulations, including solutions, suspensions, emulsions, syrups, elixirs, and the like. Rectal administration can be accomplished using, e.g., ointments, suppositories, enemas, and the like.

For oral preparations, the compounds can be used alone or in combination with appropriate additives to make tablets, powders, granules, or capsules, for example, with conventional additives, such as lactose, mannitol, corn starch, or potato starch; with binders, such as crystalline cellulose, cellulose derivatives, acacia, corn starch, or gelatins; with disintegrators, such as corn starch, potato starch, or sodium carboxymethylcellulose; with lubricants, such as talc or magnesium stearate; and, if desired, with diluents, buffering agents, moistening agents, preservatives, and/or flavoring agents.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes, and polyethylene glycols, which melt at body temperature, yet are solidified at room temperature.

Unit dosage forms for oral or rectal administration, such as syrups, elixirs, and suspensions may be provided wherein each dosage unit, for example, teaspoonful, tablespoonful, tablet or suppository, contains a predetermined amount of the compounds of the present disclosure. Similarly, unit dosage forms for injection or intravenous administration may comprise one or more compounds in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present disclosure depend on the particular compound or compounds employed and the effect to be achieved, and the pharmacodynamics associated with each compound in the subject.

In practicing the methods of the present disclosure, an effective amount of a suitably-formulated enteral composition described herein may be administered to a subject via any desired route of administration. Such administration may be a single administration, or may be repeated one or more times in order to establish and/or maintain a desired concentration of the compound in a target tissue of a subject.

In some instances, the methods may include administering an MAOI compound to a subject in conjunction with one or more additional therapies to treat a skin neoplasm, i.e., one or more additional skin neoplasm active agents. As such, the compositions of the present disclosure may be used alone to treat a skin neoplasm, or alternatively, for example, they may be used in combination with or as an adjunct to conventional treatment with other medications, e.g., anti-neoplastic agents. The compositions and methods of the present disclosure may generally be used in combination with any anti-neoplastic agents, such as conventional and/or experimental chemotherapeutic agents (i.e., anti-neoplastic agents), radiation treatments, and the like.

Anti-neoplastic agents that may be used in combination with the MAOI compounds and methods of the present disclosure include, but are not limited to, e.g., alkylating agents and platinum compounds (e.g., cisplatin, carboplatin, oxaliplatin, mechlorethamine, cyclophosphamide, chlorambucil, ifosfamide), anti-metabolic agents (e.g., purine and pyrimidine analogues, antifolates), anthracyclines (doxorubicin, daunorubicin, valrubicin, idarubicin, epirubicin), cytotoxic antibiotics (actinomycin, bleomycin, plicamycin, mitomycin), monoclonal antibodies (e.g., Alemtuzumab, Bevacizumab, Cetuximab, Gemtuzumab, Ibritumomab, Panitumumab, Rituximab, Tositumomab, and Trastuzumab, kinase inhibitors (e.g., imatinib, erlotinib, gefitinib, plant alkaloids and terpenoids, topoisomerase inhibitors (e.g., camptothecins, irinotecan, topotecan, amsacrine, etoposide, etoposide phosphate, teniposide), vinca alkaloids (e.g., vincristine, vinblastine, vinorelbine, vindesine), taxanes (e.g., paclitaxel, taxol, docetaxel), podophyllotoxins, epipodophyllotoxins, and the like.

In certain embodiments, the subject methods may include a diagnostic step. Individuals may be diagnosed as being in need of the subject methods using any convenient protocol suitable for use in diagnosing the presence of a skin neoplasm, such as visual diagnosis, biopsy, dermatoscopy, etc. In addition, individuals may be known to be in need of the subject methods, e.g., they are suffering from a skin neoplasm. Methods of the present disclosure may further include assessing the efficacy of the treatment protocol, which may be performed using any convenient protocol, e.g., by monitoring the rate of regression and/or progression of the skin neoplasm conditions (such as by using the diagnosis protocols, e.g., as described above).

Methods of the invention are suitable for use with a variety of different subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). In some embodiments, the subjects, e.g., patients, are humans.

Kits

Kits for use in practicing certain methods described herein are also provided. In certain embodiments, the kits include one or more compositions as described above. In some embodiments, the kits further comprise an additional composition, such as an anti-neoplastic agent, that may also be used to treat a subject. Such kits may provide the compositions in separate formulations, or may provide the compositions in a co-formulation. In a given kit that includes two or more compositions, the compositions may be individually packaged or present within a common container.

In certain embodiments, the kits may further include instructions for practicing the subject methods or means for obtaining the same (e.g., a website URL directing the user to a webpage that provides the instructions), where these instructions may be printed on a substrate, where the substrate may be one or more of: a package insert, the packaging, reagent containers and the like. In the subject kits, the one or more components may be present in the same or in different containers, as may be convenient or desirable.

The following examples are offered by way of illustration and not by way of limitation. Specifically, the following examples are of specific embodiments for carrying out the present invention. The examples are for illustrative purposes only, and are not intended to limit the scope of the present invention in any way.

EXAMPLES

I. Materials and Methods

A. Preparation of Compositions

Formulations for transdermal compositions were prepared by mixing stock solutions of each of the mixture components in organic solvents (typically 30-60 wt % solid content in ethyl acetate, methanol and/or ethanol), followed by a mixing process. Once a homogeneous mixture was formed, the solution was cast on a release liner (siliconized polyester sheet of 2-3 mils) and dried at 65°-80° C. for 10-90 minutes. The adhesive films were laminated to a PET backing.

Formulations for oral administration were prepared by dissolving the composition in sterile water at a concentration of 1.5 mg/mL. Solutions were prepared fresh on each day of dosing.

B. Cell Lines for Animal Studies

The SKMEL28 human melanoma cell line was obtained from ATCC and grown according to the vendor's instructions until a log growth phase was obtained. The cells were harvested from the culture vessel, washed once and re-suspended in serum free medium and matrigel mixed at a 1:1 ratio.

C. Animals Used

Female athymic (nu/nu) mice were used for in vivo animal studies. The mice were 7-8 weeks old at the time of tumor implantation. Six groups of mice were included in the study, with 10 animals in each group. The total number of animals used in the study (as well as the group size and number of groups) was the appropriate number for proper characterization of tumor growth characteristics and for comparison between treatment groups with both routes of administration studied based on historically established conventions in the industry for the type of study performed, as well as previous experience with related test articles.

D. Tumor Model Preparation for Animal Studies

Mice were inoculated subcutaneously in the scapular area in a volume of 0.2 mL containing ~10×10$^6$ SKMEL28 cells. The sub-scapular area was chosen because some of the tumor groups were treated with transdermal patches and this location would be more consistently covered by the patch in comparison to the flank/hip area. In addition, mice were not able to directly chew on the patch when placed in the scapular area.

E. Tumor Volumes in Animal Studies

Tumor dimensions were measured twice a week with digital calipers and tumor volumes were calculated from the dimensions with the formula: Tumor Volume (m)=$(a^2 \times b/2)$; where "a" was the smallest dimension and "b" was the largest dimension. Once tumors reached approximately 100 mm$^3$, animals were assigned to treatment groups such that there were no significant differences between groups for either tumor volume or body weight as measured by One-way ANOVA. Test article treatment was initiated on the same day as assignment to treatment groups. Tumor dimensions were measured and tumor volumes calculated every three days (at the same time as patch removal and application) for 21 days. Tumor volumes were also transformed into percent change in tumor volume using the formula: Percent Change TV=$(TV_i-TV_o)/TV_o \times 100\%$; where TV was tumor volume, $TV_i$ was the tumor volume at the measurement time and $TV_o$ was the initial tumor volume. Differences between treatment groups for both the raw tumor volumes and percent changes in tumor volume versus time data sets were evaluated with Two-way ANOVAs. Pair-wise differences between the no treatment and test article treatment groups on each measurement day were evaluated with post hoc Bonferroni's T-tests. In order to evaluate the growth rates of the tumors between treatments, straight lines were fitted through the different data sets (percent change in tumor volumes versus time) by least squares regression. Slopes of the lines were compared initially between all groups and then in a pair-wise fashion between the "no treatment" and "test article" treated groups using an F-test. In all cases, P values less than 0.05 were considered significant.

F. Body Weights in Animal Studies

Body weights were measured prior to dosing and every three days concurrent with tumor measurements for both patch removal/application and oral dosing. Body weights were transformed into percent change in body weight using the formula: Percent Change BW=$(BW_i-BW_o)/BW_o \times 100\%$; where BW was body weight, $BW_i$ was the body weight at the measurement time and $BW_o$ was the initial body weight. Differences between treatment groups for both the raw body weight and percent change in body weight versus time data sets were evaluated with Two-way ANOVAs. Pair-wise differences between the no treatment and test article treatment groups on each measurement day were evaluated with post hoc Bonferroni's T-tests. P values less than 0.05 were considered significant.

G. Test Article Administration in Animal Studies

Test article administrations were initiated on the same day as treatment group assignments and according to the Experimental Grouping Table. Rasagiline administration consisted of either oral gavage (15 mg/kg PO, daily for 21 days) or topical transdermal patch treatment. Cisplatin was administered once-weekly via intraperitoneal injection. Transdermal patches were applied to the intrascapular (i.e., directly over the tumor) and chest areas and maintained in position with a single BandAid™. Fresh patches were applied to the same locations every third day. The skin was cleaned prior to the first patch application with clorehexadene and as necessary prior to repeat applications. Any cleaning of the patch application area was documented in the study records. Mice were conscious and lightly restrained for patch removal and application. The patches were 0.75 or 1.2 in$^2$. An amendment to the protocol specified that the 1.2 in$^2$ patches would no longer be used because tenting of the patch was observed resulting in poor adhesion over the tumor area and, therefore, two 0.75 in$^2$ patches would be applied (one on the dorsal and one on the ventral surface of the animal). In order to control for any compressive effects on tumor growth, all mice in the study wore a BandAid™, irrespective of the treatment group.

H. Blood Collection for Pharmacokinetic Analysis in Animal Studies

At the end of the 21-day treatment duration, 2 animals from each group were euthanized at each of the following time points by isoflurane inhalation (0.5, 1, 2, 4, 8, and 24 hours after the last administration of the test articles including the application of fresh transdermal patches). For the 15 mg/kg PO Rasagiline group, two mice were bled twice (cheek bleed and terminal cardiac) so that ten mice could supply blood samples for six time points. Blood samples were collected from these animals via cardiac puncture into blood collection tubes containing lithium heparin. The blood samples were processed within 30 minutes of collection by centrifugation to prepare plasma samples. The plasma was separated from the cellular fraction and frozen on dry ice. Plasma samples were stored at −80° C. until they were shipped to an analytical laboratory designated by the Sponsor.

I. Terminal Procedures in Animal Studies

In addition to blood sampling the animals were examined for any lung or liver metastases at euthanasia.

J. Animals Found Dead or Moribund

The percentage of animal mortality and time of death was recorded for every group in the study. Animals were defined as moribund and euthanized if one or more of the following criteria were met: prolonged or excessive pain or distress as defined by clinical observations such as: prostration, hunched posture, paralysis/paresis, distended abdomen, ulcerations, abscesses, seizures and/or hemorrhages; loss of more than 20% of their body weight; if the tumor volumes exceeded 2,000 mm$^3$ or the tumors ulcerated, bled or produced exudates.

K. Transdermal Flux Tests

Human cadaver skin was used and epidermal layers (stratum corneum and epidermis) were separated from the full-thickness skin to form a skin membrane. Samples were die-cut with an arch punch to a final diameter of about 2.0 cm$^2$. The release liner was removed and the system was placed on top of the epidermis/stratum corneum with the drug adhesive layer facing the stratum corneum. Gentle pressure was applied to effect good contact between the adhesive layer and stratum corneum. The donor and receptor sides of the Franz cell were clamped together and the receptor solution containing a phosphate buffer at pH 6.5 was added to the Franz cell. The Franz cells were kept at 33° C. for the duration of the experiment. Samples of the receptor solution were taken at regular intervals and the active agent concentration was measured by HPLC. The removed receptor solution was replaced with fresh solution to maintain the sink conditions. The flux was calculated from the slope of cumulative amounts of the drug in the receiver compartment versus time plot.

II. Results

A. Inoculation and Randomization

Figure 2:
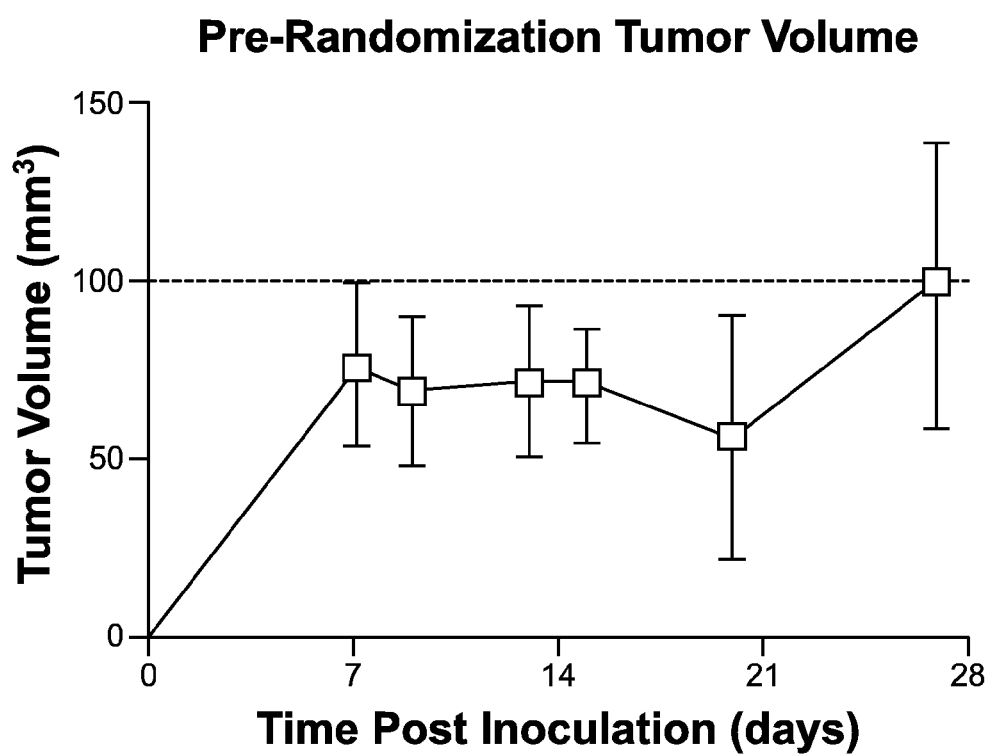
FIG. 2 is a graph of the tumor volumes in the subcutaneous space of the animals following tumor inoculation, prior to assignment to treatment groups. Data points represent the mean body weights, error bars represent standard deviations and lines are connecting lines between mean values. The dotted horizontal line represents the tumor volume criteria for assignment to treatment groups.
Figure 3:
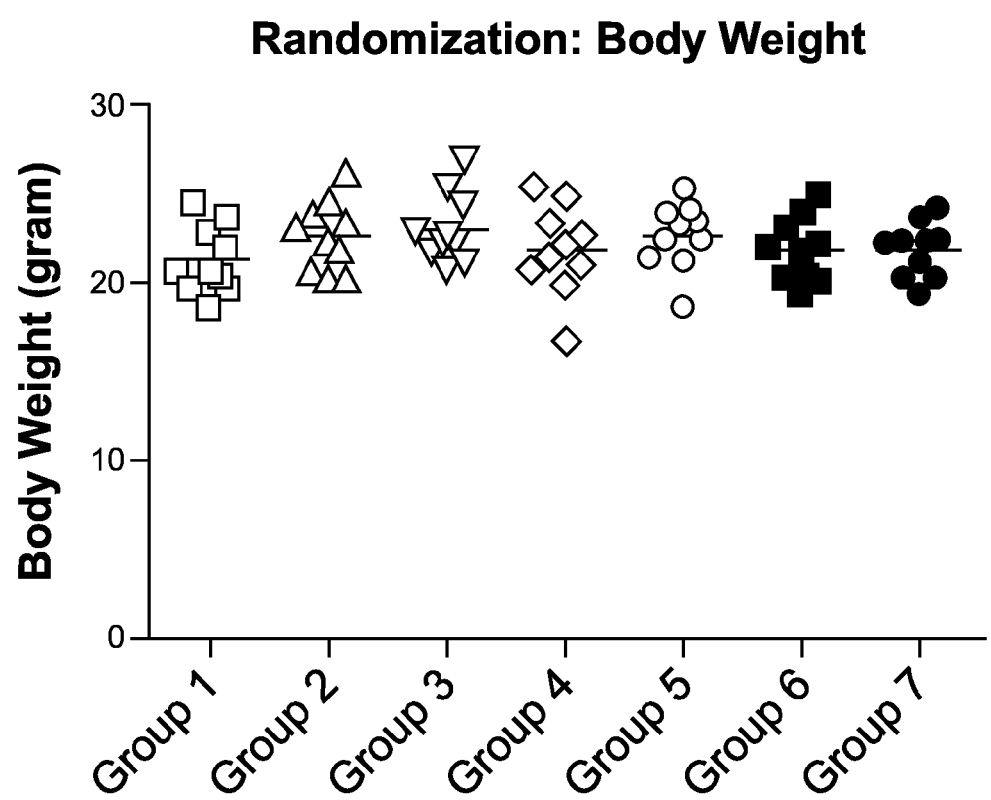
FIG. 3 is a graph of the body weights of the animals assigned to the different treatment groups at randomization. Data points represent the individual values and horizontal lines represent mean values for each group. No significant differences between groups were observed.
Figure 4:
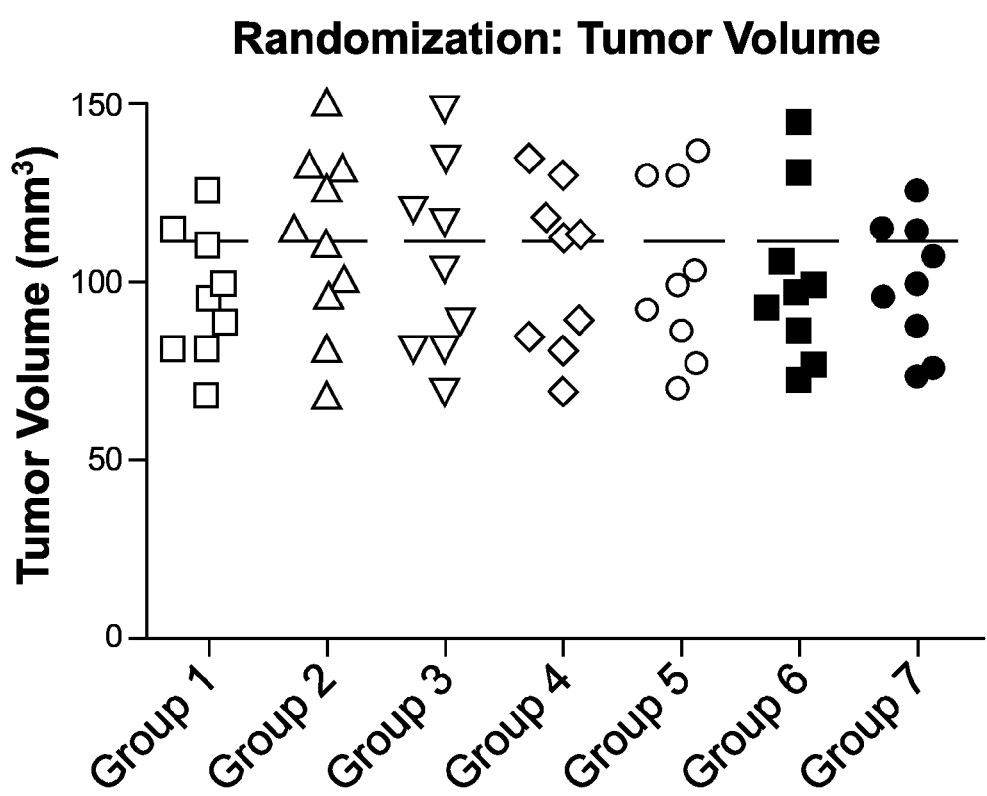
FIG. 4 is a graph of the tumor volumes in the subcutaneous space of the animals assigned to the different treatment groups at randomization. Data points represent the individual values and horizontal lines represent mean values for each group. No significant differences between groups were observed.

Female athymic mice were monitored for body weight and tumor volume at regular intervals after inoculation with 10×10$^6$ SKMEL28 cells. In general, animals slightly gained weight (FIG. 1) as the inoculated cells developed into solid tumors (FIG. 2). On the 28$^{th}$ day after inoculation, mice were randomized into groups such that there were no significant differences in average body weight (FIG. 3, Table 1) or tumor volume (FIG. 4, Table 1; one-way ANOVA).

TABLE 1

Results of the One-way ANOVAs evaluating body weights (BW) and tumor volumes (TV) between treatment groups at randomization. P values less than 0.05 were considered significant.

| One-was analysis of variance | BW | TV |
|---|---|---|
| P value | 0.3776 | 1.000 |
| Are means significantly different (P < 0.05)? | No | No |
| Number of groups | 7 | 7 |
| F | 1.091 | 0.000438 |
| R squared | 0.09413 | 4.17E−05 |

B. Survival

Figure 5:
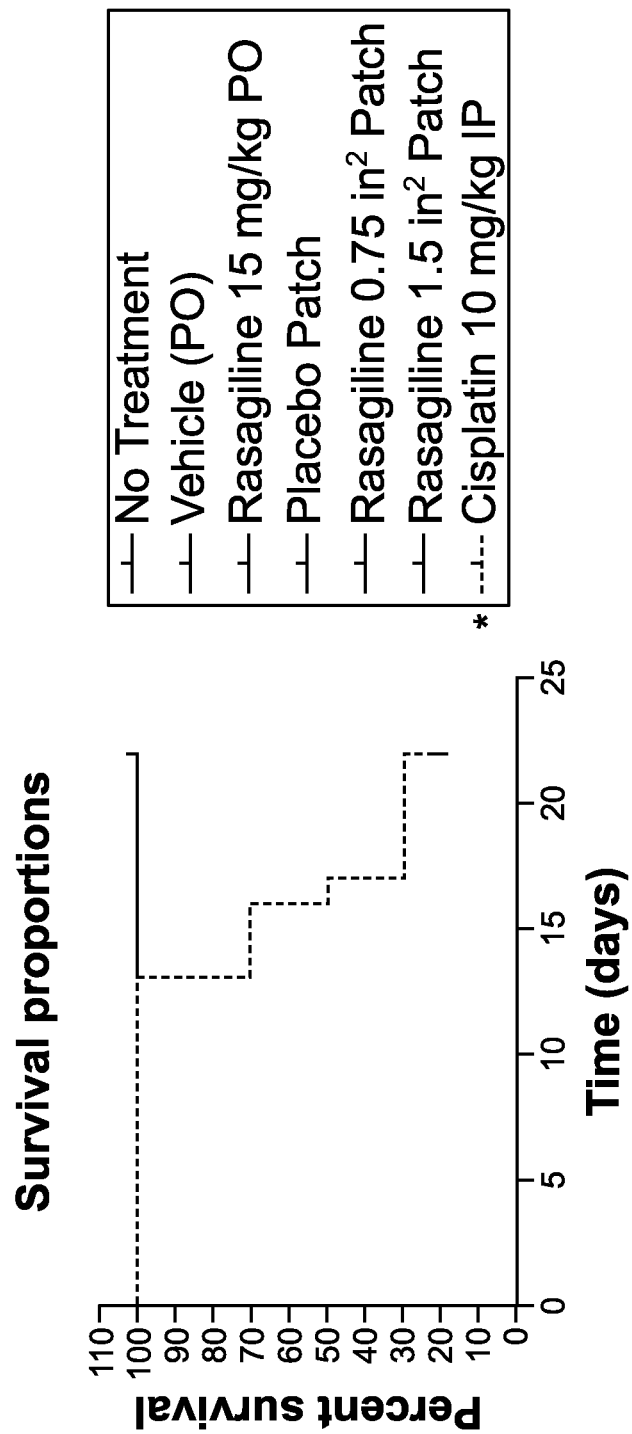
FIG. 5 is a graph of the survival proportions of the animals in each group in the study. Lines represent stepwise survival curves. * indicates P<0.05 compared to the No Treatment group.

All animals from groups 1-6 (untreated, vehicle, and rasagiline groups) survived to the end of the study, however 7 out of the 10 animals from group 7 (cisplatin, 10 mg/kg) died. Three animals (912, 941 and 973) died on Day 13, two animals (943 and 944) died on Day 16 and two animals (947 and 973) died on Day 17 of study. Survival of the animals was recorded for the entire experiment. If an animal died or was euthanized due to morbidity during the experiment, its day of death was designated as "1". If an animal survived the entire time course of the experiment, the last day of observation was designated as a "0". Survival data was analyzed using a Kaplan-Meier Survival analysis and survival curves were compared using a Log-rank test. P values less than 0.05 were considered significant. Survival proportions are shown in FIG. 5. Data are shown in Tables 2, 3, and 4.

TABLE 2

Experimental Grouping Table.

| Group ID | Test Articles | Dosage | Regimen | Route of Administration | Total Tx | Number of mice/group |
|---|---|---|---|---|---|---|
| 1 | No treatment | N/A | N/A | N/A | 21 days | 10 |
| 2 | Vehicle | N/A | Daily, for 21 days | PO | | |
| 3 | Rasagiline | 15 mg/kg | | | | |
| 4 | Placebo | N/A | Every 3 days for 21 days | Transdermal | | |
| 5 | Rasagiline | 0.75 in$^2$ | | | | |
| 6 | Rasagiline | 1.2 in$^2$ | | | | |
| 7 | Cisplatin | 10 mg/kg | Every 7 days for 21 days | Intraperitoneal | | |

TABLE 3

Results of the Logrank test comparing the survival of the Cisplatin treated group versus the No Treatment group (other comparisons were not made since all other animals survived the entire time course of the experiment).

| Logrank Test | No Treatment v. Cisplatin |
|---|---|
| Chi square | 10.86 |
| df | 1 |
| P value | 0.001 |
| Are the survival curves significantly different? | Yes |

TABLE 4

Results of the two-way ANOVA evaluating differences in body weight versus time between groups. The lower table contains results of the post hoc Bonferroni's T-tests evaluating pair wise differences between the No Treatment groups and other test article groups on each measurement day. The Cisplatin treated group was not included in the analysis due to their low survival rate.

| Two-way ANOVA | BW | | |
|---|---|---|---|
| Source of Variation | % of total variation | P value | Significant? |
| Interaction | 4.42 | 0.8107 | No |
| Treatment | 21.82 | P < 0.0001 | Yes |
| Time | 1.04 | 0.4933 | No |

| Source of Variation | Df | Sum-of-squares | F |
|---|---|---|---|
| Interaction | 30 | 80.5 | 0.7655 |
| Treatment | 5 | 397.6 | 22.69 |
| Time | 6 | 18.97 | 0.9021 |
| Residual | 378 | 1325 | N/A |

| Bonferroni post-tests No Treatment vs. Vehicle | | | |
|---|---|---|---|
| Day | Difference | t$^a$ | P value |
| 1 | 1.39 | 1.66 | P > 0.05 |
| 4 | 1.52 | 1.815 | P > 0.05 |
| 7 | 1.25 | 1.493 | P > 0.05 |
| 10 | 1.25 | 1.493 | P > 0.05 |
| 13 | 1.29 | 1.541 | P > 0.05 |
| 16 | 0.7 | 0.836 | P > 0.05 |
| 22 | 0.83 | 0.9913 | P > 0.05 |

| Vehicle vs. Rasagiline PO | | | |
|---|---|---|---|
| Day | Difference | t | P value |
| 1 | 0.4100 | 0.4897 | P > 0.05 |
| 4 | −0.1100 | 0.1314 | P > 0.05 |
| 7 | 0.2200 | 0.2627 | P > 0.05 |
| 10 | 0.3400 | 0.4061 | P > 0.05 |
| 13 | 0.1700 | 0.2030 | P > 0.05 |
| 16 | 0.2800 | 0.3344 | P > 0.05 |
| 22 | −0.5500 | 0.6569 | P > 0.05 |

| No Treatment vs. Placebo | | | |
|---|---|---|---|
| 1 | 0.62 | 0.7405 | P > 0.05 |
| 4 | −1.08 | 1.29 | P > 0.05 |
| 7 | −1.23 | 1.469 | P > 0.05 |
| 10 | −1.89 | 2.257 | P > 0.05 |
| 13 | −1.55 | 1.851 | P > 0.05 |
| 16 | −1.12 | 1.338 | P > 0.05 |
| 22 | −0.65 | 0.7763 | P > 0.05 |

| Placebo vs. 0.75 in$^2$ Patch | | | |
|---|---|---|---|
| 1 | 0.7400 | 0.8838 | P > 0.05 |
| 4 | 1.120 | 1.338 | P > 0.05 |
| 7 | 1.440 | 1.720 | P > 0.05 |
| 10 | 1.070 | 1.278 | P > 0.05 |
| 13 | 0.7700 | 0.9196 | P > 0.05 |

TABLE 4-continued

Results of the two-way ANOVA evaluating differences in body weight versus time between groups. The lower table contains results of the post hoc Bonferroni's T-tests evaluating pair wise differences between the No Treatment groups and other test article groups on each measurement day. The Cisplatin treated group was not included in the analysis due to their low survival rate.

| | | | |
|---|---|---|---|
| 16 | 0.8300 | 0.9913 | P > 0.05 |
| 22 | 0.9400 | 1.123 | P > 0.05 |
| Placebo vs. 1.5 in² Patch | | | |
| 1 | −0.05000 | 0.05972 | P > 0.05 |
| 4 | 0.5300 | 0.6330 | P > 0.05 |
| 7 | −0.3000 | 0.3583 | P > 0.05 |
| 10 | −0.4800 | 0.5733 | P > 0.05 |
| 13 | −0.4300 | 0.5136 | P > 0.05 |
| 16 | −0.9100 | 1.087 | P > 0.05 |
| 22 | −0.5400 | 0.6449 | P > 0.05 |

("t" refers to Student's T-test with the Bonferroni correction applied to the alpha value for multiple comparisons).

C. Body Weights

Figure 6:
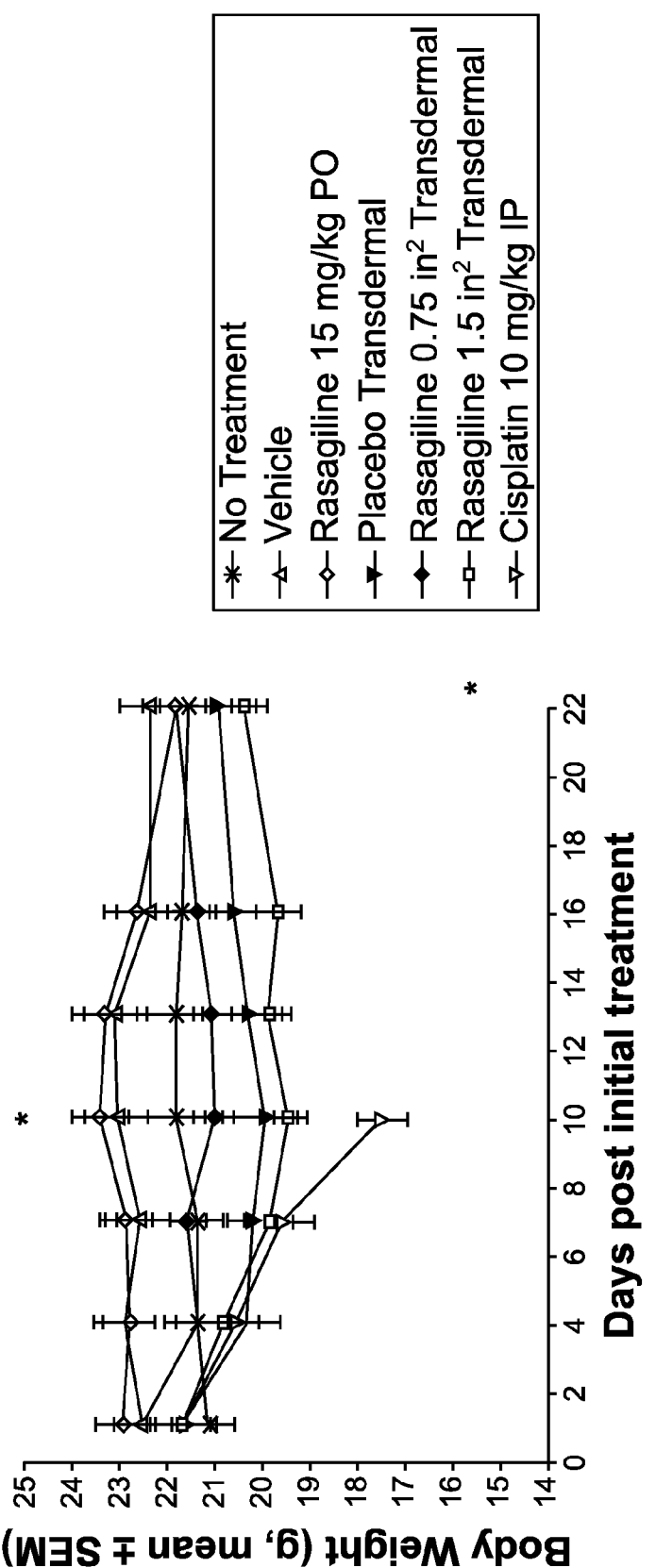
FIG. 6 is a graph of the body weights of the animals in each group versus time. Data points represent man values, error bars represent standard error of the means and lines are connecting lines between mean values. * indicates P<0.05 compared to the No Treatment group on that given day.
Figure 7:
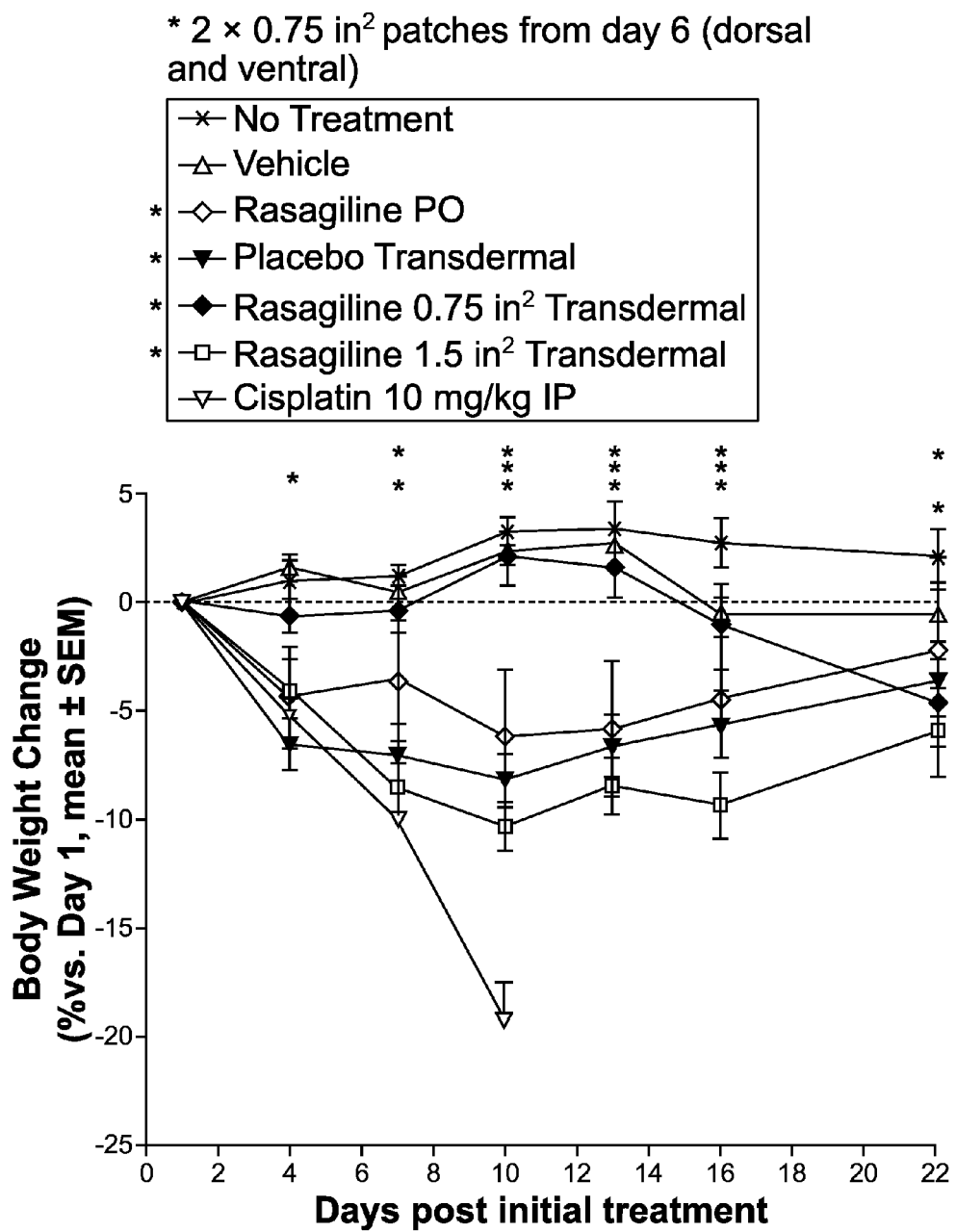
FIG. 7 is a graph of the percent changes in body weights of the animals from each group versus time. Data points represent mean values, error bars represent standard errors of the means and lines are connecting lines between mean values. * indicates P<0.05 compared to the No Treatment group on that given day.
Figure 11:
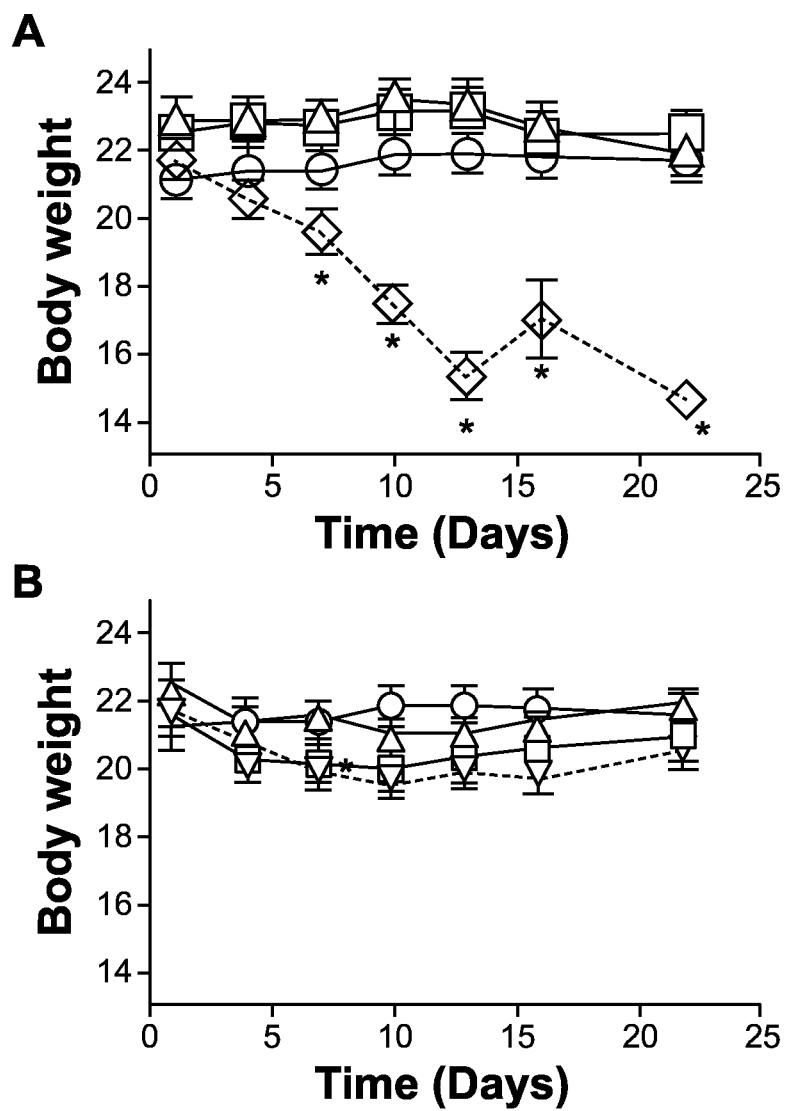
FIG. 11A is a graph of animal weight (g) over the treatment duration for oral (vehicle—□ or rasagiline—Δ) or IP (cisplatin—◊) delivery relative to untreated animals—○. Values represent the mean and standard error of the mean (SEM) of 10 animals with the exception of the cisplatin group (n=3-10, due to mortality). Statistical significance indicated by (*) and represents p<0.05.
FIG. 11B is a graph of animal weight (g) over the treatment duration for transdermal (placebo patch—■, one patch—▲ or two patches—▼) administration relative to untreated animals—● for the administration period. Values represent the mean and standard error of the mean (SEM) of 10 animals with the exception of the cisplatin group (n=3-10, due to mortality). Statistical significance indicated by (*) and represents p<0.05.
Figure 12:
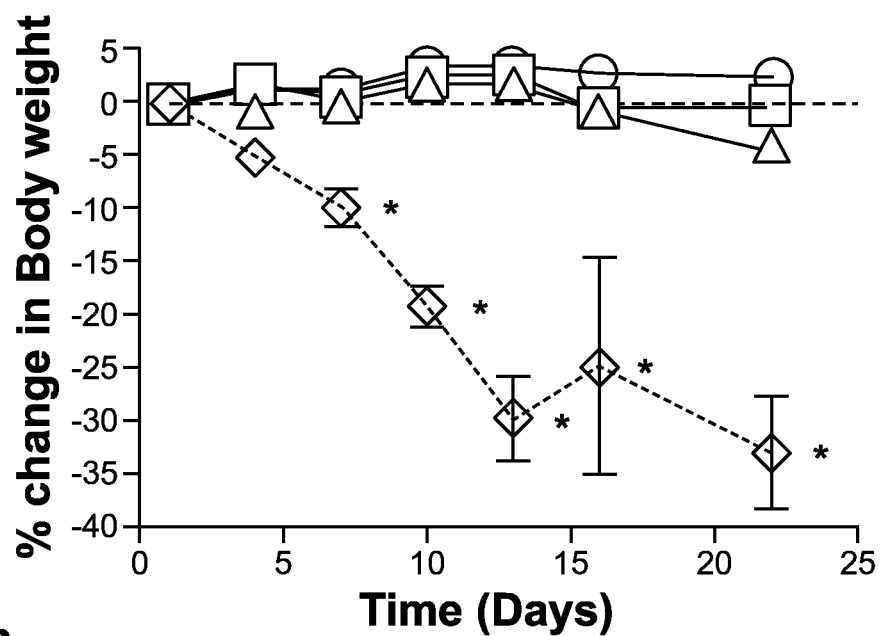
FIG. 12A is a graph of the percent change in body weight relative to the initial weight (g) over the treatment duration for oral (vehical—□ or rasagiline—Δ) or IP (cisplatin—◊) delivery relative to untreated animals—○. Values represent the mean and SEM of 10 animals with the exception of the cisplatin group (n=3-10, due to mortality). Statistical significance indicated by (*) and represents p<0.05.
FIG. 12B is a graph of the percent change in body weight relative to the initial weight (g) over the treatment duration for transdermal (placebo patch—■, one patch—▲ or two patches—▼) administration relative to untreated animals—●) for the administration period. Values represent the mean and SEM of 10 animals with the exception of the cisplatin group (n=3-10, due to mortality). Statistical significance indicated by (*) and represents p<0.05.
Figure 12:
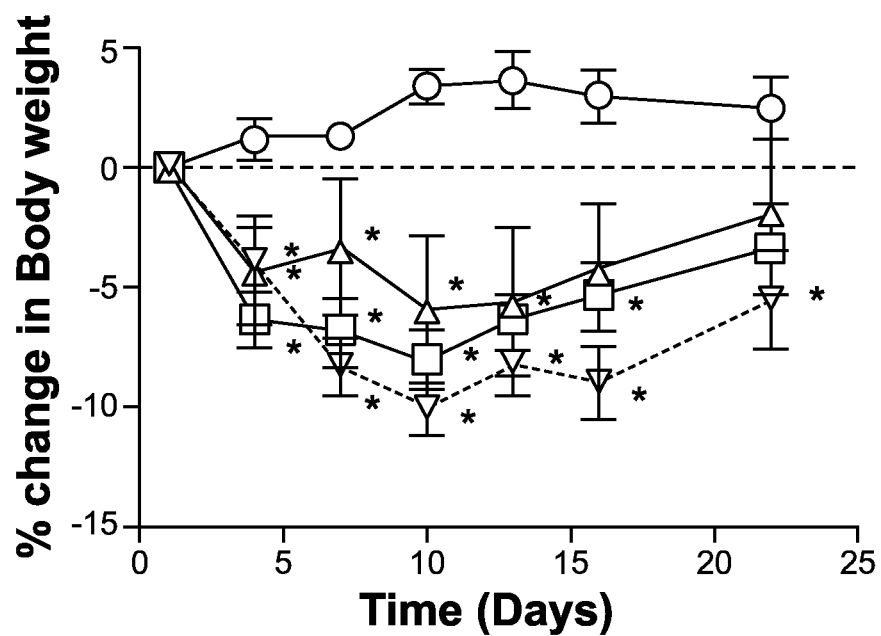

Body weights were measured every three days concurrent with tumor measurements and just prior to removal/application of transdermal patches. Data are shown in FIG. 6. Absolute body weights were transformed to percent change from the start of treatment. The percent change in body weight was significantly impacted by treatment (FIG. 7). Thus, oral administration of rasagiline steadily reduced body weight from day 13 onwards, reaching significance on the last day of the experiment when compared with the no treatment group. Although treatment with all of the transdermal patches (including placebo) significantly reduced body weight until day 10 (when compared with the no treatment group), the fact that similar weight loss was also recorded in the placebo transdermal patch group suggests that it was not related to transdermal rasagiline exposure. These reductions in body weight largely resolved themselves from day 10 to the end of the experiment and only remained significantly reduced in the 1.5 in² rasagiline patch-treated animals compared to no treatment animals (FIG. 7, Table 5). Cisplatin-treated animals were removed from the analysis because of their low survival rate. Data are shown in Tables 5, 6, 7, and 8. Absolute body weight over the treatment duration for animals dosed with oral rasagiline is shown in FIG. 11A. Absolute body weight over the treatment duration for animals receiving transdermal administration of rasagiline is shown in FIG. 11B. Percent change in body weight over the treatment duration for animals dosed with oral rasagiline is shown in FIG. 12A. Percent change in body weight over the treatment duration for animals receiving transdermal administration of rasagiline is shown in FIG. 12B.

TABLE 5

Results of the Two-way ANOVA evaluating differences in percent changes in body weights versus time between groups. The lower table contains results of the post hoc Bonferroni's T-tests evaluating pair wise differences between the No Treatment groups and other test article groups on each measurement day. The Cisplatin treated group was not included in the analysis due to their low survival rate.

| Two-way ANOVA | % BW | | |
|---|---|---|---|
| Source of Variation | % of total variation | P value | Significant? |
| Interaction | 10.6 | 0.0002 | Yes |
| Treatment | 28.6 | P < 0.0001 | Yes |
| Time | 2.34 | 0.0208 | Yes |

| Source of Variation | Df | Sum-of-squares | Mean square | F |
|---|---|---|---|---|
| Interaction | 30 | 1615 | 53.84 | 2.285 |
| Treatment | 5 | 4358 | 871.5 | 36.98 |
| Time | 6 | 357.1 | 59.51 | 2.525 |
| Residual | 378 | 8909 | 23.57 | N/A |

| Bonferroni post-tests | | | |
|---|---|---|---|
| No Treatment vs. Vehicle | | | |
| Day | Difference | t | P value |
| 1 | 0 | 0 | P > 0.05 |
| 4 | 0.574 | 0.2644 | P > 0.05 |
| 7 | −0.7791 | 0.3589 | P > 0.05 |
| 10 | −0.866 | 0.3989 | P > 0.05 |
| 13 | −0.749 | 0.345 | P > 0.05 |
| 16 | −3.35 | 1.543 | P > 0.05 |
| 22 | −2.687 | 1.238 | P > 0.05 |
| Vehicle vs. Rasagiline PO | | | |
| 1 | 0.0000 | 0.0000 | P > 0.05 |
| 4 | −2.229 | 1.027 | P > 0.05 |
| 7 | −0.7052 | 0.3248 | P > 0.05 |
| 10 | −0.2490 | 0.1147 | P > 0.05 |
| 13 | −1.053 | 0.4850 | P > 0.05 |
| 16 | −0.4240 | 0.1953 | P > 0.05 |
| 22 | −4.072 | 1.876 | P > 0.05 |
| No Treatment vs. Placebo | | | |
| 1 | 0 | 0 | P > 0.05 |
| 4 | −7.564 | 3.484 | P < 0.01 |

TABLE 5-continued

Results of the Two-way ANOVA evaluating differences in percent changes in body weights versus time between groups. The lower table contains results of the post hoc Bonferroni's T-tests evaluating pair wise differences between the No Treatment groups and other test article groups on each measurement day. The Cisplatin treated group was not included in the analysis due to their low survival rate.

| | | | |
|---|---|---|---|
| 7 | −8.253 | 3.801 | $P < 0.01$ |
| 10 | −11.44 | 5.271 | $P < 0.001$ |
| 13 | −10.03 | 4.618 | $P < 0.001$ |
| 16 | −8.288 | 3.817 | $P < 0.01$ |
| 22 | −5.866 | 2.702 | $P > 0.05$ |
| Placebo vs. 0.75 in² Patch | | | |
| 1 | 0.0000 | 0.0000 | $P > 0.05$ |
| 4 | 2.090 | 0.9628 | $P > 0.05$ |
| 7 | 3.533 | 1.627 | $P > 0.05$ |
| 10 | 2.062 | 0.9497 | $P > 0.05$ |
| 13 | 0.7890 | 0.3634 | $P > 0.05$ |
| 16 | 1.163 | 0.5357 | $P > 0.05$ |
| 22 | 1.441 | 0.6637 | $P > 0.05$ |
| Placebo vs. 1.5 in² Patch | | | |
| 1 | 0.0000 | 0.0000 | $P > 0.05$ |
| 4 | 2.521 | 1.161 | $P > 0.05$ |
| 7 | −1.488 | 0.6856 | $P > 0.05$ |
| 10 | −2.095 | 0.9649 | $P > 0.05$ |
| 13 | −1.809 | 0.8332 | $P > 0.05$ |
| 16 | −3.742 | 1.724 | $P > 0.05$ |
| 22 | −2.199 | 1.013 | $P > 0.05$ |

TABLE 6

Results of the Two-way ANOVA evaluating differences in tumor volumes versus time between groups. The lower table contains results of the post hoc Bonferroni's T-tests evaluating pair wise differences between the No Treatment groups and other test article groups on each measurement day. The Cisplatin treated group was not included in the analysis due to their low survival rate.

| Two-way ANOVA | TV | | |
|---|---|---|---|
| Source of Variation | % of total variation | P value | Significant? |
| Interaction | 1.88 | 0.6683 | No |
| Treatment | 1.87 | 0.0001 | Yes |
| Time | 69.01 | $P < 0.0001$ | Yes |

| Source of Variation | Df | Sum-of-squares | Mean square | F |
|---|---|---|---|---|
| Interaction | 30 | 552100 | 18400 | 0.869 |
| Treatment | 5 | 550800 | 110200 | 5.202 |
| Time | 6 | 20280000 | 3380000 | 159.6 |
| Residual | 378 | 8005000 | 21180 | N/A |

Bonferroni post-tests
No Treatment vs. Vehicle PO

| Day | Difference | t | P value |
|---|---|---|---|
| 1 | −0.1627 | 0.0025 | $P > 0.05$ |
| 4 | −1.455 | 0.02236 | $P > 0.05$ |
| 7 | 6.854 | 0.1053 | $P > 0.05$ |
| 10 | 11.41 | 0.1753 | $P > 0.05$ |
| 13 | 21.12 | 0.3245 | $P > 0.05$ |
| 16 | 1.534 | 0.02357 | $P > 0.05$ |
| 22 | −21.8 | 0.3349 | $P > 0.05$ |
| Vehicle vs. Rasagiline (15 mg/kg PO) | | | |
| 1 | −0.2606 | 0.004004 | $P > 0.05$ |
| 4 | −15.03 | 0.2309 | $P > 0.05$ |
| 7 | −40.95 | 0.6292 | $P > 0.05$ |
| 10 | −50.83 | 0.7811 | $P > 0.05$ |
| 13 | −92.36 | 1.419 | $P > 0.05$ |
| 16 | −128.8 | 1.979 | $P > 0.05$ |
| 22 | −154.4 | 2.372 | $P > 0.05$ |

TABLE 6-continued

Results of the Two-way ANOVA evaluating differences in tumor volumes versus time between groups. The lower table contains results of the post hoc Bonferroni's T-tests evaluating pair wise differences between the No Treatment groups and other test article groups on each measurement day. The Cisplatin treated group was not included in the analysis due to their low survival rate.

| No Treatment vs. Placebo Transdermal | | | |
|---|---|---|---|
| 1 | −0.1443 | 0.002217 | P > 0.05 |
| 4 | 18.6 | 0.2858 | P > 0.05 |
| 7 | 6.436 | 0.0989 | P > 0.05 |
| 10 | 13.39 | 0.2058 | P > 0.05 |
| 13 | 36.39 | 0.5591 | P > 0.05 |
| 16 | 35.76 | 0.5495 | P > 0.05 |
| 22 | 52.77 | 0.8109 | P > 0.05 |
| Placebo vs. Rasagiline 0.75 in$^2$ Patch | | | |
| 1 | 0.002754 | 0.00004232 | P > 0.05 |
| 4 | −7.783 | 0.1196 | P > 0.05 |
| 7 | 4.720 | 0.07252 | P > 0.05 |
| 10 | −18.69 | 0.2871 | P > 0.05 |
| 13 | −53.58 | 0.8233 | P > 0.05 |
| 16 | −135.5 | 2.082 | P > 0.05 |
| 22 | −223.1 | 3.428 | P < 0.01 |
| Placebo vs. Rasagiline 1.5 in$^2$ Patch | | | |
| 1 | 0.01410 | 0.0002166 | P > 0.05 |
| 4 | −38.91 | 0.5978 | P > 0.05 |
| 7 | −15.42 | 0.2369 | P > 0.05 |
| 10 | −44.17 | 0.6787 | P > 0.05 |
| 13 | −115.5 | 1.774 | P > 0.05 |
| 16 | −186.3 | 2.863 | P > 0.05 |
| 22 | −269.9 | 4.148 | P < 0.001 |

TABLE 7

Results of the Two-way ANOVA evaluating differences in percent changes in tumor volumes versus time between groups. The lower table contains results of the post hoc Bonferroni's T-tests evaluating pair wise differences between the No Treatment groups and other test article groups on each measurement day. The Cisplatin treated group was not included in the analysis due to their low survival rate.

| Two-way ANOVA | % TV | | |
|---|---|---|---|
| Source of Variation | % of total variation | P value | Significant? |
| Interaction | 1.98 | 0.7568 | No |
| Treatment | 2.04 | 0.0002 | Yes |
| Time | 65.02 | P < 0.0001 | Yes |

| Source of Variation | Df | Sum-of-squares | Mean square | F |
|---|---|---|---|---|
| Interaction | 30 | 586500 | 19550 | 0.8072 |
| Treatment | 5 | 602400 | 120500 | 4.975 |
| Time | 6 | 19220000 | 3204000 | 132.3 |
| Residual | 378 | 9154000 | 24220 | |

| Bonferroni post-tests No Treatment vs. Vehicle PO | | | |
|---|---|---|---|
| Day | Difference | t | P value |
| 1 | 0 | 0 | P > 0.05 |
| 4 | −4.279 | 0.06148 | P > 0.05 |
| 7 | 0.703 | 0.0101 | P > 0.05 |
| 10 | −6.468 | 0.09294 | P > 0.05 |
| 13 | −6.826 | 0.09808 | P > 0.05 |
| 16 | −45.2 | 0.6495 | P > 0.05 |
| 22 | −61.48 | 0.8833 | P > 0.05 |
| Vehicle vs. Rasagiline 15 mg/kg PO | | | |
| 1 | 0.0000 | 0.0000 | P > 0.05 |
| 4 | −12.56 | 0.1804 | P > 0.05 |
| 7 | −36.19 | 0.5200 | P > 0.05 |
| 10 | −42.92 | 0.6167 | P > 0.05 |
| 13 | −71.82 | 1.032 | P > 0.05 |

TABLE 7-continued

Results of the Two-way ANOVA evaluating differences in percent changes in tumor volumes versus time between groups. The lower table contains results of the post hoc Bonferroni's T-tests evaluating pair wise differences between the No Treatment groups and other test article groups on each measurement day. The Cisplatin treated group was not included in the analysis due to their low survival rate.

| | | | |
|---|---|---|---|
| 16 | −98.35 | 1.413 | P > 0.05 |
| 22 | −153.3 | 2.203 | P > 0.05 |
| *No Treatment vs. Placebo Transdermal* | | | |
| 1 | 0 | 0 | P > 0.05 |
| 4 | 13.81 | 0.1984 | P > 0.05 |
| 7 | 4.633 | 0.06657 | P > 0.05 |
| 10 | 7.404 | 0.1064 | P > 0.05 |
| 13 | 36.67 | 0.5269 | P > 0.05 |
| 16 | 32.05 | 0.4605 | P > 0.05 |
| 22 | 38.56 | 0.5541 | P > 0.05 |
| *Placebo vs. Rasagiline 0.75 in$^2$ Patch* | | | |
| 1 | 0.0000 | 0.0000 | P > 0.05 |
| 4 | −1.119 | 0.01608 | P > 0.05 |
| 7 | 12.01 | 0.1725 | P > 0.05 |
| 10 | −6.402 | 0.09199 | P > 0.05 |
| 13 | −45.26 | 0.6503 | P > 0.05 |
| 16 | −107.7 | 1.547 | P > 0.05 |
| 22 | −178.6 | 2.566 | P > 0.05 |
| *Placebo vs. Rasagiline 1.5 in$^2$ Patch* | | | |
| 1 | 0.0000 | 0.0000 | P > 0.05 |
| 4 | −32.39 | 0.4654 | P > 0.05 |
| 7 | −18.37 | 0.2640 | P > 0.05 |
| 10 | −46.51 | 0.6683 | P > 0.05 |
| 13 | −127.6 | 1.834 | P > 0.05 |
| 16 | −204.7 | 2.942 | P > 0.05 |
| 22 | −293.6 | 4.219 | P < 0.001 |

TABLE 8

Results of the least squares linear fit to the percent changes in tumor volume versus time data sets. The lower table contains the results of the F-tests comparing the slopes of the lines.
Equation: Polynomial: First Order (straight line) Y = Intercept + Slope * X

| | No Treatment | Vehicle | Rasagiline 15 mg/kg PO | Placebo Transdermal | Rasagiline Small Patch (0.75 in$^2$) | Rasagiline Large Patch (1.5 in$^2$) | Cisplatin 10 mg/kg IP |
|---|---|---|---|---|---|---|---|
| Best-fit values | | | | | | | |
| INTERCEPT | −84.55 | −70.53 | −53.92 | −85.86 | −39.04 | −37.08 | −9.996 |
| SLOPE | 36.96 | 33.92 | 26.64 | 38.91 | 29.94 | 24.32 | 13.16 |
| Std. Error | | | | | | | |
| INTERCEPT | 32.51 | 25.54 | 18.5 | 34 | 54.76 | 24.03 | 14.59 |
| SLOPE | 2.623 | 2.061 | 1.493 | 2.743 | 4.418 | 1.939 | 1.717 |
| Goodness of Fit | | | | | | | |
| Degrees of Freedom | 68 | 68 | 68 | 68 | 68 | 68 | 48 |
| R$^2$ | 0.7449 | 0.7994 | 0.8242 | 0.7474 | 0.4031 | 0.6982 | 0.5503 |

| | | No Treatment vs. | | | | | |
|---|---|---|---|---|---|---|---|
| Comparison of Fits by F-tests | All curves | Vehicle PO | Rasagiline 15 mg/kg PO | Placebo Transdermal | Rasagiline Small Patch (0.75 in$^2$) | Rasagiline Large Patch (1.5 in$^2$) | Cisplatin 10 mg/kg IP |
| Null hypothesis | SLOPE same for all data sets | SLOPE same for all data sets | SLOPE same for all data sets | SLOPE same for all data sets | SLOPE same for all data sets | SLOPE same for all data sets | SLOPE same for all data sets |
| Alternative hypothesis | SLOPE different for each data set | SLOPE different for each data set | SLOPE different for each data set | SLOPE different for each data set | SLOPE different for each data set | SLOPE different for each data set | SLOPE different for each data set |

TABLE 8-continued

Results of the least squares linear fit to the percent changes in tumor volume versus time data sets. The lower table contains the results of the F-tests comparing the slopes of the lines.
Equation: Polynomial: First Order (straight line) Y = Intercept + Slope * X

| P value | P < 0.0001 | =0.3642 | =0.0008 | =0.6086 | =0.1741 | =0.0002 | P < 0.0001 |
|---|---|---|---|---|---|---|---|
| Conclusion (alpha = 0.05) | Reject null hypothesis | Do not reject null hypothesis | Reject null hypothesis | Do not reject null hypothesis | Do not reject null hypothesis | Reject null hypothesis | Reject null hypothesis |
| Preferred model | SLOPE different for each data set | SLOPE same for all data sets | SLOPE different for each data set | SLOPE same for all data sets | SLOPE same for all data sets | SLOPE different for each data set | SLOPE different for each data set |
| F (DFn, DFd) | 6.876 (6,456) | 0.8291 (1,136) | 11.69 (1,136) | 0.2635 (1,136) | 1.867 (1,136) | 15.01 (1,136) | 31.65 (1,116) |

P values are expressed as "p=" when the result of the Bonferroni T-test did not reach p < 0.0001.

D. Tumor Volumes

Figure 8:
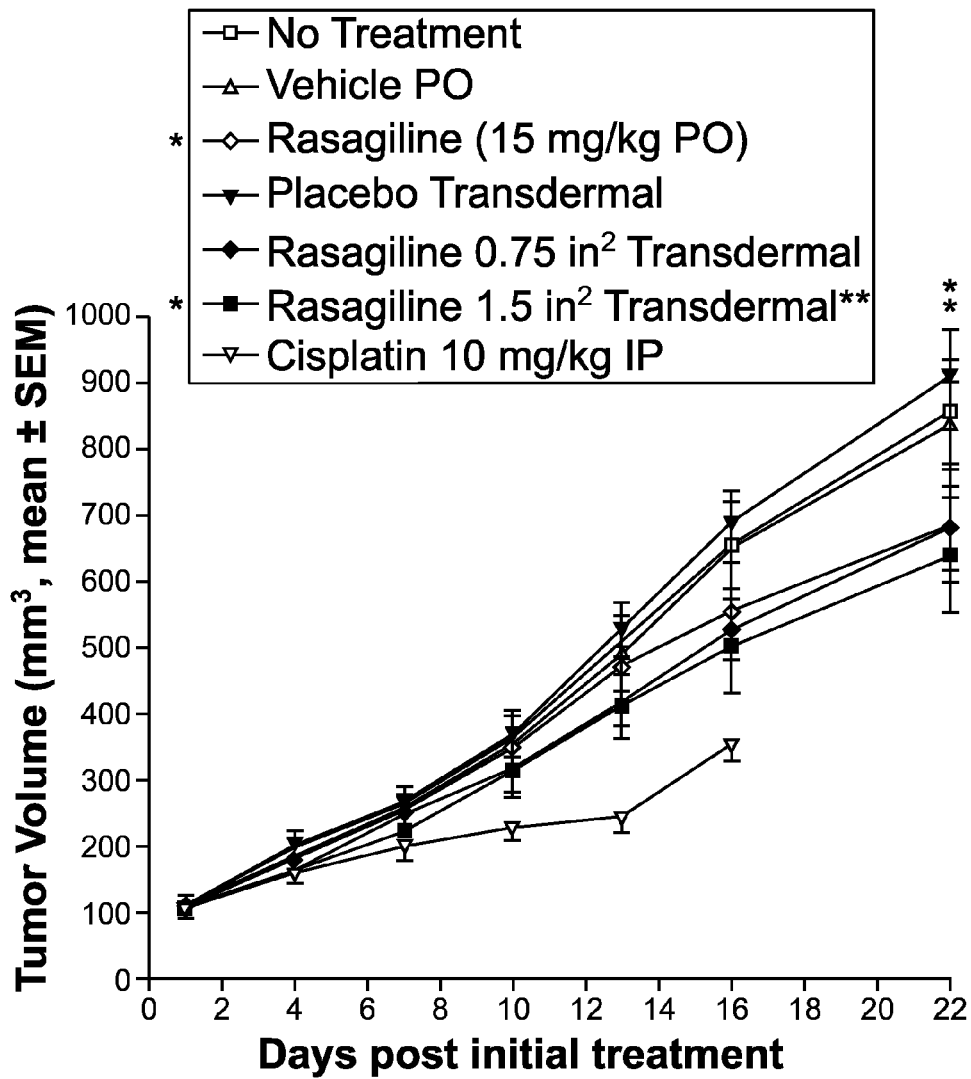
FIG. 8 is a graph of the tumor volumes of the animals from each group versus time. Data points represent mean values, error bars represent standard errors of the means and lines are connecting lines between mean values. * indicates P<0.05 compared to the No Treatment group on that given day.
Figure 9:
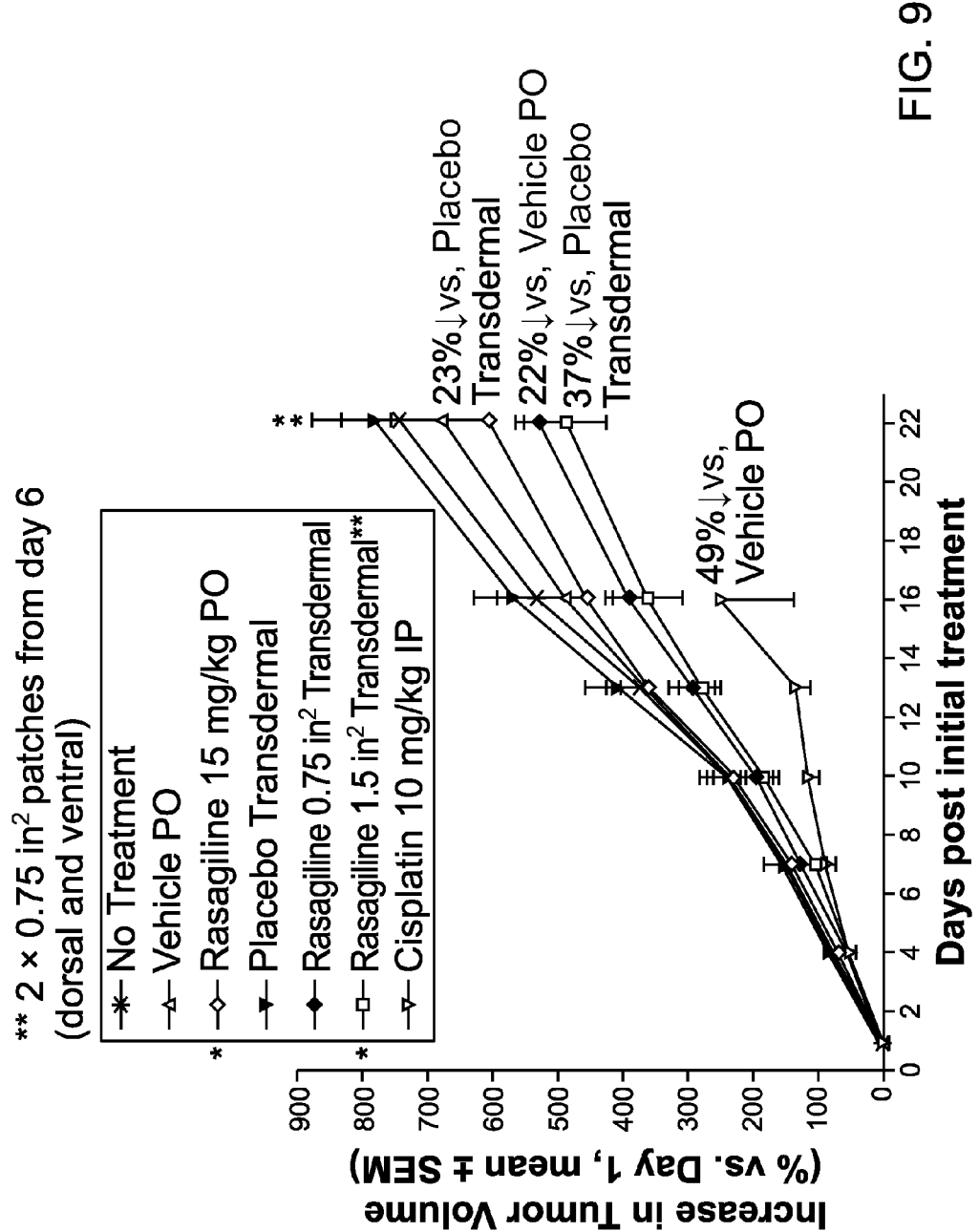
FIG. 9 is a graph of the percent changes in tumor volumes of the animals from each group versus time. Data points represent mean values, error bars represent standard errors of the means and lines are connecting lines between mean values. * indicates P<0.05 compared to the No Treatment group on that given day. Percent reductions in percent changes in tumor volumes compared to the appropriate vehicle groups are written next to the last data point in several groups.
Figure 13:
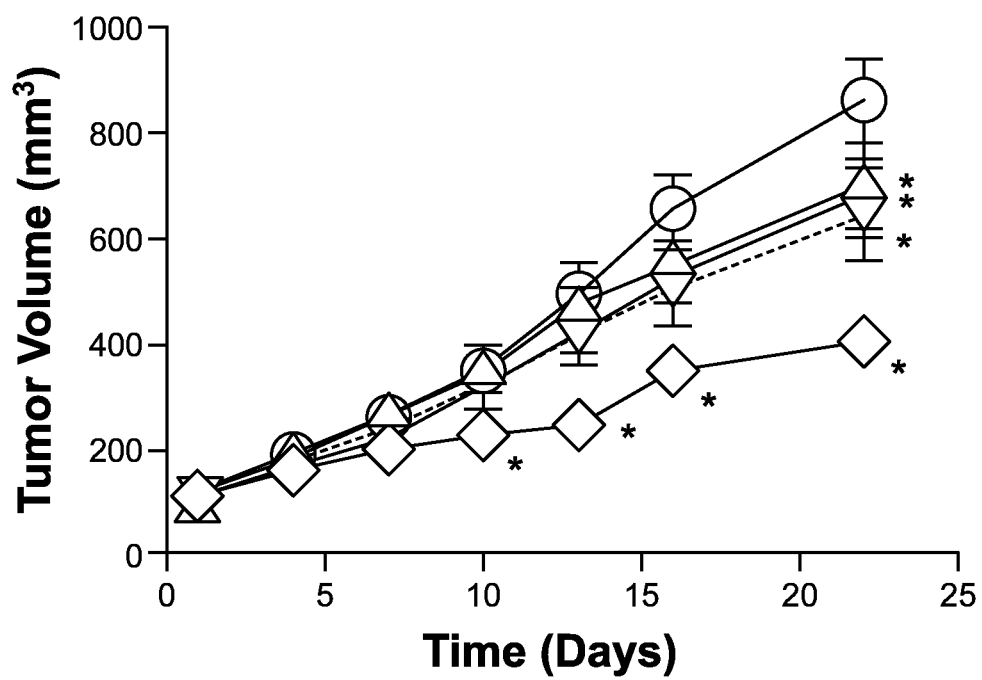
FIG. 13 is a graph of absolute SKMEL28 tumor volumes ($mm^3$) over the treatment duration for animals administered oral rasagiline—■, one patch—▲, or two patches—▼ and relative to IP cisplatin—♦ and untreated animals—○. Values represent the mean and SEM of 10 animals with the exception of the cisplatin group (n=3-10, due to mortality). Statistical significance indicated by (*) and represents p<0.05.
Figure 14:
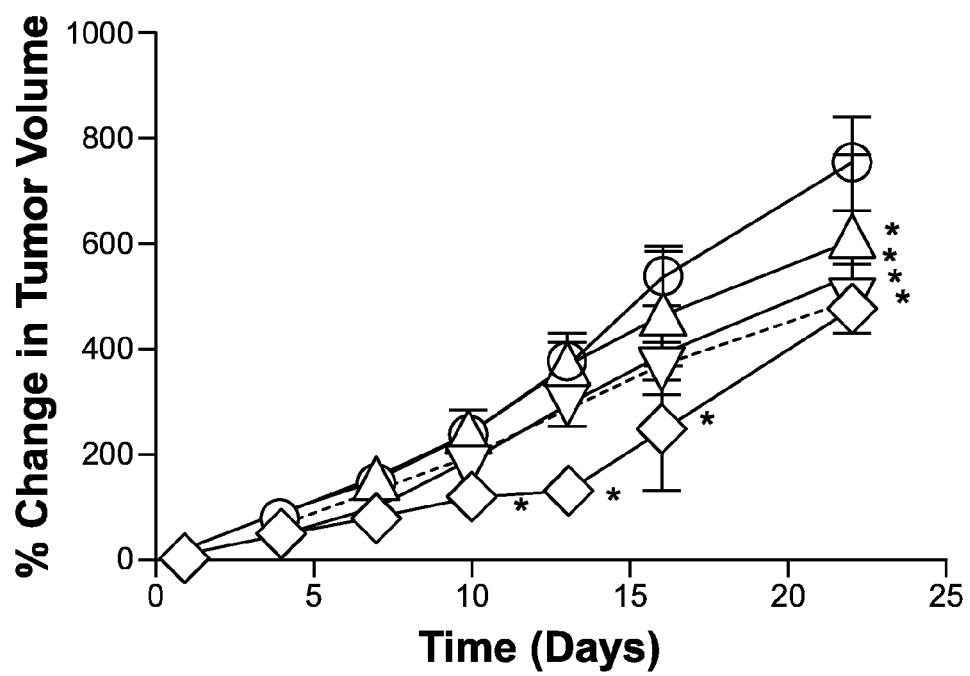
FIG. 14 is a graph of the percent change in SKMEL28 tumor volumes ($mm^3$) over the treatment duration for animals administered oral rasagiline—■, one patch—▲, or two patches—▼ and relative to IP cisplatin—♦ and untreated animals—○. Values represent the mean and SEM of 10 animals with the exception of the cisplatin group (n=3-10, due to mortality). Statistical significance indicated by (*) and represents p<0.05.

Tumor dimensions were measured and tumor volumes calculated twice a week for the remainder of the experiment. Data are shown in FIG. 8. Tumor volumes were transformed into percent change in tumor volume using the formula: Percent Change TV=($TV_i$-$TV_o$)/$TV_o$×100%; where TV was tumor volume, $TV_i$ was the tumor volume at the measurement time and $TV_o$ was the initial tumor volume. These data are shown in FIG. 9. Differences between treatment groups for both the raw tumor volumes and percent changes in tumor volume versus time data sets were evaluated with two-way ANOVAs. Treatment with rasagiline by oral gavage resulted in 22% reduction in percent change in tumor volume compared to the oral vehicle control. Treatment with rasagiline by 0.75 $in^2$ and 1.5 $in^2$ transdermal patches resulted in 23% and 37% reductions in percent change in tumor volume compared to the transdermal placebo, respectively. Cisplatin treatment resulted in a 49% reduction in the percent change in tumor volumes compared to the oral vehicle treatment prior to death of the majority of the animals (FIG. 9). Absolute tumor volumes ($mm^3$) over the treatment duration are shown in FIG. 13. Percent change in tumor volume ($mm^3$) over the treatment duration is shown in FIG. 14.

E. PK Results

Figure 15:
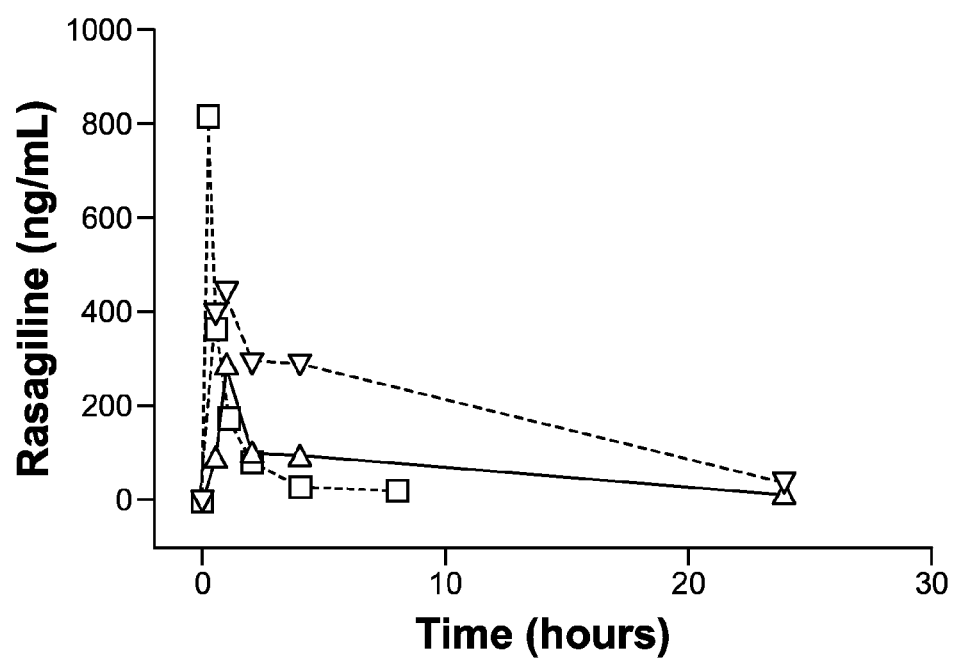
FIG. 15 is a graph of plasma rasagiline concentration versus time for samples collected after the last administration of oral rasagiline—■, one patch—▲, or two patches—▼. Values represent the mean of two animals at each timepoint. Baseline values determined from vehicle or placebo patch-treated animals (<0.5 ng/mL).

To compare rasagiline exposure by both dosing routes, blood was collected from two animals at each time point by sparse sampling techniques via cardiocentesis prior to euthanasia. Two samples were collected each from two animals in the oral dose group by collecting the first sample from the submandibular vein at 0.25 hours and cardiocentesis at eight hours. Blood was collected from animals administered oral rasagiline at 0.25, 0.5, 1, 2, 4 and 8 hours after the last oral dose. Animals administered the transdermal patches had blood collected at 0.5, 1, 2, 4, and 24 hours on the last application day. Blood collected from animals in the naïve, vehicle, and placebo patch groups determined baseline values and were used for pre-dose levels. No rasagiline concentrations were detected in naïve, vehicle, or placebo patch groups. Mean values for each time point within the rasagiline groups were used to calculate the mean $AUC_{(0-t)}$ value. The $AUC_{(0-8)}$ derived for the oral rasagiline group was multiplied by three to estimate the $AUC_{(0-24)}$ exposure. The ratio of $AUC_{(0-24)}$ for each of the baseline transdermal groups was divided by the estimated oral $AUC_{(0-24)}$ to compare exposures between the two dosing routes. The mean maximal plasma concentration after oral rasagiline administration was 899 ng/mL at 15 minutes, achieving an estimated exposure after 24 hours of 2,322 ng/mL×hr. After transdermal administration of one patch, the maximum plasma concentration was ~287 ng/mL at one hour with an exposure after 24 hours of 1,639 ng/mL×hr. With two patches, the exposure increased relatively dose proportionately with a maximum plasma concentration of 449 ng/mL at one hour and an exposure after 24 hours of 4,695 ng/mL×hr. An $AUC_{(0-24)}$ exposure comparison between one and two transdermal patches with the oral route revealed a ratio of 0.7 and 2.0, respectively. Rasagiline concentration as a function of time is shown in FIG. 15.

TABLE 9

Mean rasagiline plasma concentrations (ng/mL)[a].

| Time (h) | Oral rasagiline (15 mg/kg) | Transdermal rasagiline (1-048 $in^2$) | Transdermal rasagiline (2-0.48 $in^2$) |
|---|---|---|---|
| 0.25 | 899.0 | NA | NA |
| 0.5 | 370.5 | 97.7 | 423.5 |
| 1 | 215.5 | 286.5 | 449.0 |
| 2 | 82.5 | 102.5 | 317.0 |
| 4 | 28.4 | 94.1 | 298.0 |
| 8 | 19.9 | NA | NA |
| 24 | NA | 18.7 | 39.3 |

NA, not applicable to group.
[a]Animals administered the vehicle and placebo patch had plasma levels <0.5 ng/mL.

TABLE 10

Summary of rasagiline plasma concentrations.

| Formulation | Mean Tmax (h) | Mean Cmax (ng/mL) | Mean $AUC_{(0-24)}$ (ng/mL × h) | $AUC_{(0-24)}$ ratio with mean oral AUC |
|---|---|---|---|---|
| Oral rasagiline (15 mg/kg) | 0.25 | 899.0 | 774.1 | 1.0 |
| Transdermal rasagiline (1-048 $in^2$) | 1.0 | 286.5 | 1639 | 0.7 |
| Transdermal rasagiline (2-0.48 $in^2$) | 1.0 | 449.0 | 4695 | 2.0 |

AUC, area under the curve.

TABLE 11

Summary of rasagiline concentrations in various tissues after oral administration (0.45 mg/kg)[a].

| Tissue | Maximum % of dose | Time to maximal exposure |
|---|---|---|
| Muscle | 24.11 | 0.25 |
| Liver | 13.20 | 0.25 |
| Skin | 13.20 | 0.25 |

TABLE 11-continued

Summary of rasagiline concentrations in various tissues after oral administration (0.45 mg/kg)[a].

| Tissue | Maximum % of dose | Time to maximal exposure |
|---|---|---|
| Small intestine | 8.76 | 0.25 |
| Fat | 8.47 | 0.25 |
| Stomach | 4.73 | 0.5 |
| Whole Blood | 4.54 | 0.25 |
| Kidneys | 3.89 | 0.25 |
| Large intestine | 1.83 | 1 |
| Lung | 1.46 | 0.25 |

[a]Data derived from NDA 02161.

F. Findings

Following inoculation, mice were assigned to treatment groups such that the average group tumor volume was 100 mm$^3$ and treatment initiated for 21 days. Transdermal patches were replaced every 3 days and held in place with BandAids™. The patches used in the study were either 0.75 or 1.2 in$^2$ and applied to the dorsal (0.75, 1.2 in$^2$) and dorsal and ventral surfaces (1.5 in$^2$). Following an amendment to the protocol, the 1.2 in$^2$ patches were not used after day 6 of the study and two 0.75 in$^2$ patches were used instead (dorsal and ventral). Tumor volume and body weight were measured every three days at the same time as patch removal/application. On the last day of the experiment significant reductions in tumor growth were observed in the animals treated with rasagiline by both oral gavage and 1.5 in$^2$ patch compared to the group receiving no treatment. Tumor growth rates were also calculated and significantly slowed by rasagiline (oral gavage or 1.5 in$^2$ patch) or Cisplatin treatment versus mice with no treatment. Cisplatin was the only treatment to reduce the survival rate. The percent change in body weight was also significantly impacted by treatment. Thus, oral administration of rasagiline steadily reduced body weight from day 13 onwards, reaching significance on the last day of the experiment. Although treatment with all of the transdermal patches significantly reduced body weights until day 10, similar weight loss was recorded in the placebo transdermal patch group. After transdermal administration of one patch, the maximum plasma concentration was ~287 ng/mL at one hour with an exposure after 24 hours of 1,639 ng/mL×hr. With two patches, the exposure increased relatively dose proportionately with a maximum plasma concentration of 449 ng/mL at one hour and an exposure after 24 hours of 4,695 ng/mL×hr. An $AUC_{(0-24)}$ exposure comparison between one and two transdermal patches with the oral route revealed a ratio of 0.7 and 2.0, respectively.

Specifically, the conclusions were:

1. SKMEL28 cell derived tumors were successfully grown in the interscapular region and once these tumors reached an average volume of 100 mm$^3$ (27 days following inoculation), mice were immediately randomized into treatment groups for the start of treatment (FIG. 2). There were no concomitant reductions in body weight during this initial tumor growth phase (FIG. 1).

2. Cisplatin-treated animals had greater body weight loss and decreased survival rates than any other treatment group (FIG. 5, Table 3).

3. There was a trend towards reduced body weight for the test article-treated animals but only the animals treated with the 1.5 in$^2$ patches containing Rasagiline had a significant reduction in body weight on day 10 when absolute body weights were evaluated in comparison to the no treatment group (FIG. 6, Table 4).

4. When body weights were transformed to percent change from the start of treatment, a clear pattern of significant body weight reduction was seen with the transdermally-treated animals (including the placebo patch-treated animals). These reductions in body weight resolved themselves from day 10 to the end of the experiment and only remained significantly reduced in the 1.5 in$^2$ Rasagiline patch-treated animals compared to no treatment animals (FIG. 7, Table 5).

5. Oral treatment with rasagiline reduced body weight from day 13 onwards and this reached significance compared to the no treatment animals on the last day of the experiment (FIG. 7, Table 5).

6. Treatment with Rasagiline as either oral gavage or 1.5 in$^2$ transdermal patch significantly reduced tumor volume (absolute and percent change in tumor volume) on the last day of the experiment compared to the no treatment group (FIGS. 8, 9, Tables 6 and 7).

7. Treatment with rasagiline by oral gavage resulted in 22% reduction in percent change in tumor volume compared to the oral vehicle control. Treatment with Rasagiline by 0.75 in$^2$ and 1.5 in$^2$ transdermal patches resulted in 23% and 37% reductions in percent change in tumor volume compared to the transdermal placebo, respectively. Cisplatin treatment resulted in a 49% reduction in the percent change in tumor volumes compared to the oral vehicle treatment prior to death of the majority of the animals (FIG. 9).

Figure 10:
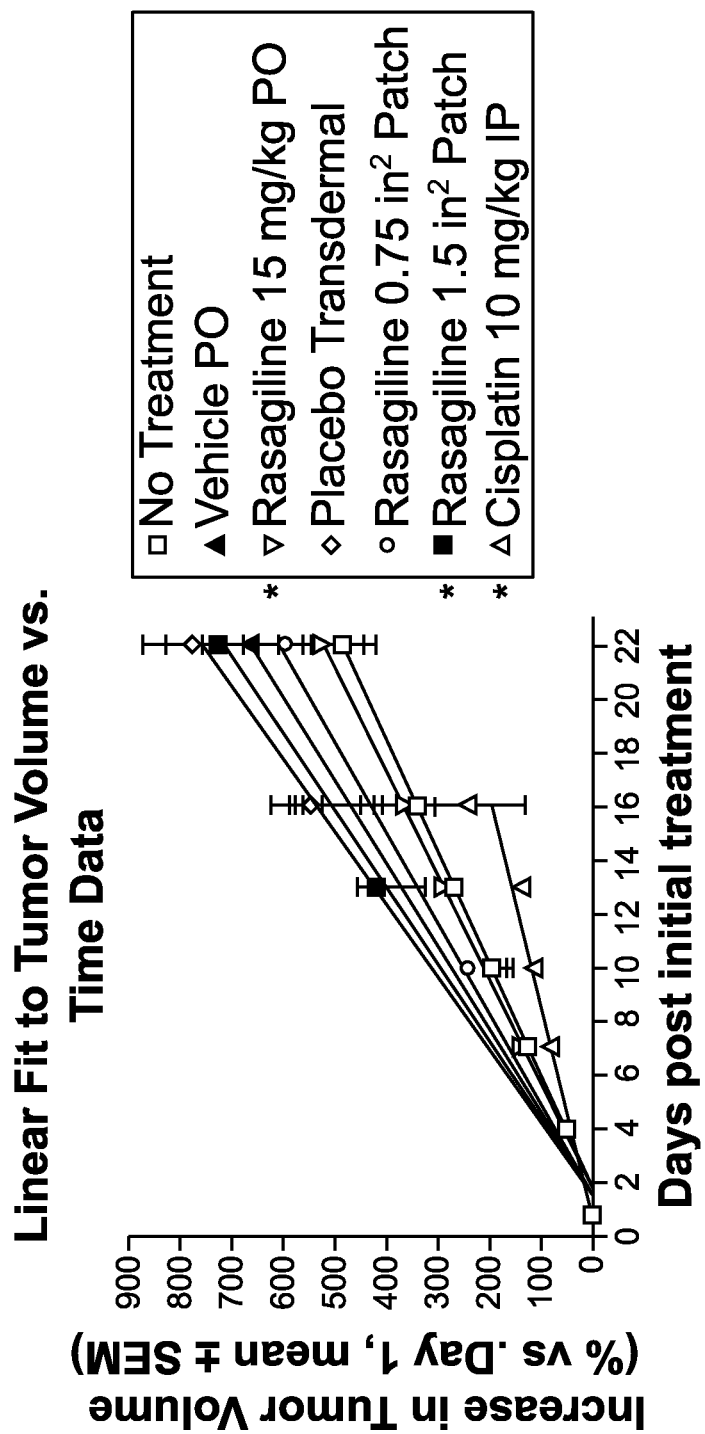
FIG. 10 is a graph of the linear curve fit to percent changes in tumor volumes of the animals from each group versus time. Data points represent mean values, error bars represent standard errors of the means and lines are best fit straight lines through the data sets. * indicates P<0.05 compared to the No Treatment group.

8. Treatment with rasagiline by oral gavage or 1.5 in$^2$ transdermal patch or with Cisplatin also significantly reduced tumor growth rates compared to the no treatment group (FIG. 10, Table 8).

9. All animals administered rasagiline, either orally or transdermally survived the dosing period.

10. Sparse blood sampling of the animals on the last day of oral administration or patch application showed detectable Rasagiline concentrations in the treatment groups and no detectable levels in the vehicle or placebo patch groups. An estimated AUC ratio, comparing the exposure over 24 hours between one or two Rasagiline transdermal patches and oral delivery revealed ratios of 0.7 and 2.0, respectively.

In conclusion, rasagiline mesylate dosed at 15 mg/kg/day via either the oral or transdermal routes (one or two 0.75 in$^2$ patches administered every three days) had comparable exposure (oral and single transdermal patch) and significantly reduced absolute tumor volumes as well as tumor growth rates in the nude mouse SKMEL28 xenograft model.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a subject having a skin neoplasm, the method consisting of:
    administering to the subject a composition comprising an effective amount of a monoamine oxidase inhibitor as the sole active agent to treat the subject for the skin neoplasm, wherein the monoamine oxidase inhibitor is a propynylaminoindan or a pharmaceutically acceptable salt thereof and is the sole active agent administered to the subject to treat the subject for the skin neoplasm.

2. The method according to claim 1, wherein the skin neoplasm is a melanocyte-derived skin neoplasm.

3. The method according to claim 2, wherein the melanocyte-derived skin neoplasm is malignant melanoma.

4. The method according to claim 1, wherein the subject has been diagnosed with the skin neoplasm.

5. The method according to claim 1, wherein the propynylaminoindan has the formula:

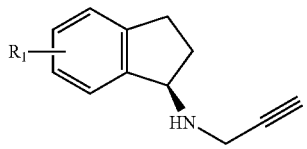

wherein $R_1$ is H, —$OR_2$, or

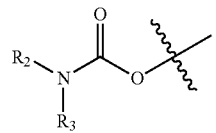

wherein $R_2$ is $C_1$-$C_4$ alkyl, and $R_3$ is H or $C_1$-$C_4$ alkyl.

6. The method according to claim 1, wherein the propynylaminoindan is rasagiline, or a pharmaceutically acceptable salt thereof.

7. The method according to claim 1, wherein the subject is human.

8. The method according to claim 1, wherein the amount of monoamine oxidase inhibitor administered to the subject ranges from 0.5 mg/kg/day to 30 mg/kg/day.

9. The method according to claim 1, wherein the amount of monoamine oxidase inhibitor administered to the subject ranges from 5 mg/kg/day to 25 mg/kg/day.

10. The method according to claim 1, wherein the amount of monoamine oxidase inhibitor administered to the subject ranges from 10 mg/kg/day to 20 mg/kg/day.

11. The method according to claim 1, wherein the amount of monoamine oxidase inhibitor administered to the subject ranges from 12.5 to 17.5 mg/kg/day.

12. The method according to claim 1, wherein the monoamine oxidase inhibitor is enterally administered to the subject.

13. The method according to claim 12, wherein the monoamine oxidase inhibitor is orally administered to the subject.

14. A method of treating a subject having a skin neoplasm the method consisting of:
    administering to the subject a composition comprising an effective amount of a monoamine oxidase inhibitor as the sole active agent to treat the subject for the skin neoplasm, wherein the monoamine oxidase inhibitor is a propynylaminoindan or a pharmaceutically acceptable salt thereof, is the sole active agent administered to the subject to treat the subject for the skin neoplasm and is administered to the subject by topically applying the composition comprising the monoamine oxidase inhibitor to the skin of the subject.

15. The method according to claim 14, wherein the composition comprises an amount of the monoamine oxidase inhibitor ranging from 0.5 mg to 1 g.

16. The method according to claim 15, wherein the composition is a solid composition configured to cover a topical area ranging in size from 10 $cm^2$ to 200 $cm^2$.

17. The method according to claim 16, wherein the amount of the monoamine oxidase inhibitor in the composition ranges from 5 mg to 90 mg.

18. The method according to claim 16, wherein the amount of the monoamine oxidase inhibitor in the composition ranges from 10 mg to 60 mg.

19. The method according to claim 16, wherein the amount of the monoamine oxidase inhibitor in the composition ranges from 15 mg to 30 mg.

20. The method according to claim 16, wherein the composition is configured to cover a topical area ranging in size from 20 $cm^2$ to 150 $cm^2$.

21. The method according to claim 16, wherein the composition is configured to cover a topical area ranging in size from 40 $cm^2$ to 140 $cm^2$.

22. The method according to claim 14, wherein the composition is applied to the skin of the subject for a period of time ranging from 1 hour to 1 week.

23. The method according to claim 14, wherein the composition is applied to the skin of the subject for a period of time ranging from 10 hours to 5 days.

24. The method according to claim 14, wherein the composition is applied to the skin of the subject for a period of time ranging from 1 day to 3 days.

25. The method according to claim 1, wherein the administering results in at least a reduction in the growth rate of the skin neoplasm.

26. The method according to claim 14, wherein the administering results in at least a reduction in the growth rate of the skin neoplasm.

* * * * *